(12) United States Patent
Quick et al.

(10) Patent No.: US 10,912,541 B2
(45) Date of Patent: *Feb. 9, 2021

(54) UNIVERSAL MEDICAL DEVICE CONTROL CONSOLE

(71) Applicant: SenoRx, Inc., Tempe, AZ (US)

(72) Inventors: Richard L. Quick, Mission Viejo, CA (US); Martin V. Shabaz, Lake Forest, CA (US); James H. Dabney, Irvine, CA (US); Daniel Kussman, Aliso Viejo, CA (US); Frank R. Louw, Carlsbad, CA (US); Paul Lubock, Monarch Beach, CA (US)

(73) Assignee: SenoRx, Inc., Franklin Lakes, NJ (US)

( * ) Notice: Subject to any disclaimer, the term of this patent is extended or adjusted under 35 U.S.C. 154(b) by 1279 days.

This patent is subject to a terminal disclaimer.

(21) Appl. No.: 14/161,218

(22) Filed: Jan. 22, 2014

(65) Prior Publication Data

US 2014/0155771 A1 Jun. 5, 2014

Related U.S. Application Data

(60) Continuation of application No. 11/980,956, filed on Oct. 31, 2007, now Pat. No. 8,652,121, which is a
(Continued)

(51) Int. Cl.
*A61B 10/02* (2006.01)
*A61B 5/01* (2006.01)
(Continued)

(52) U.S. Cl.
CPC ............... *A61B 10/02* (2013.01); *A61B 5/01* (2013.01); *A61B 5/024* (2013.01);
(Continued)

(58) Field of Classification Search
CPC ........... A61B 10/02; A61B 5/01; A61B 5/024; A61B 10/0266; A61B 10/0283;
(Continued)

(56) References Cited

U.S. PATENT DOCUMENTS 3,601,126 A 8/1971 Estes
3,903,891 A 9/1975 Brayshaw
(Continued)

FOREIGN PATENT DOCUMENTS

DE 3703218 A1 8/1988
EP 0225973 A2 6/1987
(Continued)

OTHER PUBLICATIONS

Force FX™ Electrosurgical Generator Instant Response to Tissue Density, Instant Response Technology, http://www.valleylab.com/Products/fx.html, electrosurgical Generators pp. 1-4, Jun. 21, 2000.
(Continued)

*Primary Examiner* — Aaron F Roane

(57) ABSTRACT

A control console is disclosed for controlling one or more medical devices. The control console communicates to at least one medical device, and at least one peripheral module associated with the medical device if needed. The control console has a microprocessor for processing data to direct an operation of the medical device.

20 Claims, 19 Drawing Sheets

Related U.S. Application Data division of application No. 10/847,699, filed on May 17, 2004, now abandoned.

(60) Provisional application No. 60/475,747, filed on Jun. 3, 2003.

(51) Int. Cl.
*A61B 5/024* (2006.01)
*A61B 17/00* (2006.01)
*A61B 18/14* (2006.01)
*A61B 90/00* (2016.01)

(52) U.S. Cl.
CPC ...... *A61B 10/0266* (2013.01); *A61B 10/0283* (2013.01); *A61B 18/14* (2013.01); *A61B 90/06* (2016.02); *A61B 2017/008* (2013.01); *A61B 2017/00199* (2013.01); *A61B 2017/00225* (2013.01); *A61B 2017/00482* (2013.01); *A61B 2017/00973* (2013.01)

(58) Field of Classification Search
CPC ............ A61B 90/06; A61B 18/14; A61B 2017/00199; A61B 2017/00225; A61B 2017/00482; A61B 2017/008; A61B 2017/00973
USPC ............................................................ 606/1
See application file for complete search history.

(56) References Cited

U.S. PATENT DOCUMENTS

| | | | |
|---|---|---|---|
| 3,923,063 A | 12/1975 | Andrews et al. | |
| 4,473,075 A | 9/1984 | Rexroth | |
| 4,517,976 A | 5/1985 | Murakoshi et al. | |
| 4,559,943 A | 12/1985 | Bowers | |
| 4,617,927 A | 10/1986 | Manes | |
| 4,658,819 A | 4/1987 | Harris et al. | |
| 4,739,759 A | 4/1988 | Rexroth et al. | |
| 4,781,175 A | 11/1988 | McGreevy et al. | |
| 4,878,493 A | 11/1989 | Pasternak et al. | |
| 4,961,047 A | 10/1990 | Carder | |
| 5,087,257 A | 2/1992 | Farin et al. | |
| 5,133,711 A | 7/1992 | Hagen | |
| 5,159,929 A | 11/1992 | Morris et al. | |
| 5,261,906 A | 11/1993 | Pennino et al. | |
| 5,269,780 A | 12/1993 | Roos | |
| 5,300,068 A | 4/1994 | Rosar et al. | |
| 5,383,874 A | 1/1995 | Jackson et al. | |
| 5,400,267 A | 3/1995 | Denen et al. | |
| 5,445,635 A | 8/1995 | Denen et al. | |
| 5,507,743 A | 4/1996 | Edwards et al. | |
| 5,530,960 A | 6/1996 | Parks et al. | |
| 5,530,962 A | 6/1996 | Ramey | |
| 5,558,671 A | 9/1996 | Yates | |
| 5,617,857 A * | 4/1997 | Chader | A61B 5/06 128/899 |
| 5,749,869 A | 5/1998 | Lindenmeier et al. | |
| 5,772,659 A | 6/1998 | Becker et al. | |
| 5,817,091 A | 10/1998 | Nardella et al. | |
| 5,846,236 A | 12/1998 | Lindenmeier et al. | |
| 5,849,009 A | 12/1998 | Bernaz | |
| 5,906,614 A | 5/1999 | Stern et al. | |
| 5,971,980 A | 10/1999 | Sherman | |
| 5,976,128 A | 11/1999 | Schilling et al. | |
| 5,997,535 A | 12/1999 | Betsill et al. | |
| 6,022,347 A | 2/2000 | Lindenmeier et al. | |
| 6,036,681 A | 3/2000 | Hooven | |
| 6,066,134 A | 5/2000 | Eggers et al. | |
| 6,074,386 A | 6/2000 | Goble et al. | |
| 6,117,126 A | 9/2000 | Appelbaum et al. | |
| 6,162,216 A | 12/2000 | Guziak et al. | |
| 6,228,080 B1 | 5/2001 | Gines | |
| 6,228,082 B1 | 5/2001 | Baker et al. | |
| 6,238,387 B1 | 5/2001 | Miller, III | |
| 6,370,411 B1 | 4/2002 | Osadchy et al. | |
| 6,391,024 B1 | 5/2002 | Sun et al. | |
| 6,432,065 B1 * | 8/2002 | Burdorff | A61B 10/0275 600/566 |
| 6,458,121 B1 | 10/2002 | Rosenstock et al. | |
| 6,461,350 B1 | 10/2002 | Underwood et al. | |
| 6,475,215 B1 | 11/2002 | Tanrisever | |
| 6,514,248 B1 | 2/2003 | Eggers et al. | |
| 6,620,157 B1 | 9/2003 | Dabney et al. | |
| 6,632,183 B2 | 10/2003 | Bowman et al. | |
| 6,652,520 B2 | 11/2003 | Moorman et al. | |
| 6,780,178 B2 | 8/2004 | Palanker et al. | |
| 6,939,347 B2 | 9/2005 | Thompson | |
| 6,981,941 B2 | 1/2006 | Whitman et al. | |
| 7,060,063 B2 | 6/2006 | Marion et al. | |
| 7,175,618 B2 | 2/2007 | Dabney et al. | |
| 7,976,540 B2 | 7/2011 | Daw et al. | |
| 8,231,615 B2 | 7/2012 | Daw et al. | |
| 8,475,446 B2 | 7/2013 | Daw et al. | |
| 8,652,121 B2 * | 2/2014 | Quick | A61B 10/02 606/1 |
| 2002/0026188 A1 * | 2/2002 | Balbierz | A61B 5/0071 606/41 |
| 2002/0077565 A1 | 6/2002 | Burdorff et al. | |
| 2002/0133151 A1 | 9/2002 | Hung et al. | |
| 2002/0198519 A1 | 12/2002 | Qin et al. | |
| 2003/0050628 A1 * | 3/2003 | Whitman | A61B 17/00 606/1 |
| 2003/0055419 A1 | 3/2003 | Panescu et al. | |
| 2003/0093103 A1 | 5/2003 | Malackowski et al. | |
| 2003/0130711 A1 | 7/2003 | Pearson et al. | |
| 2003/0144605 A1 | 7/2003 | Burbank et al. | |
| 2003/0171745 A1 | 9/2003 | Francischelli et al. | |
| 2003/0181898 A1 | 9/2003 | Bowers | |
| 2003/0229341 A1 | 12/2003 | Albrecht et al. | |
| 2004/0030334 A1 | 2/2004 | Quick et al. | |
| 2004/0082945 A1 | 4/2004 | Clague et al. | |
| 2004/0172017 A1 | 9/2004 | Marion et al. | |
| 2004/0181219 A1 | 9/2004 | Goble et al. | |
| 2005/0119646 A1 | 6/2005 | Scholl et al. | |
| 2007/0129716 A1 | 6/2007 | Daw et al. | |
| 2007/0255271 A1 | 11/2007 | Dabney et al. | |
| 2007/0282322 A1 | 12/2007 | Dabney et al. | |
| 2009/0030405 A1 | 1/2009 | Quick et al. | |
| 2009/0069799 A1 | 3/2009 | Daw et al. | |
| 2012/0165807 A1 | 6/2012 | Daw et al. | |
| 2013/0211398 A1 | 8/2013 | Daw et al. | |
| 2013/0317494 A1 | 8/2013 | Daw et al. | |
| 2015/0119873 A1 | 4/2015 | Daw et al. | |

FOREIGN PATENT DOCUMENTS

| | | |
|---|---|---|
| EP | 1051948 A2 | 11/2000 |
| EP | 1053719 A1 | 11/2000 |
| EP | 1053720 A1 | 11/2000 |
| EP | 1082945 A1 | 3/2001 |
| EP | 1157667 A2 | 11/2001 |
| EP | 1519472 A1 | 3/2005 |
| EP | 1527743 A2 | 5/2005 |
| GB | 2146534 A | 4/1985 |
| JP | 2002320325 A | 10/2002 |
| WO | 9315655 A1 | 8/1993 |
| WO | 9639088 A1 | 12/1996 |
| WO | 9807378 A1 | 2/1998 |
| WO | 9814129 A1 | 4/1998 |
| WO | 0224082 A2 | 3/2002 |
| WO | 2004110294 A1 | 12/2004 |
| WO | 2005060849 A1 | 7/2005 |

OTHER PUBLICATIONS

NEW! Force EZ™ Electrosurgical Generator Instant Response to Tissue Density, Instant Response Technology, http://www.valleylab.com/PRODUCTS/fx.html, Electrosurgical Generators pp. 1-4, Jun. 21, 2000.

(56) References Cited

OTHER PUBLICATIONS

Amplifiermodule 1-30MHz 150Watts, LCF Enterprises RF Power Amplifiers, www.lcfamps.com, pp. 1-2, 1998.
International Search Report for PCT/US2004/016143 dated Nov. 5, 2004.

* cited by examiner

1240

| OPENING |
|---|
| PLEASE WAIT |
| READY |

1246

| BIOPSY AREA OPEN |
|---|
| TO CLOSE BIOPSY AREA, PRESS SAMPLE TO CLOSE QUICKLY, PRESS SAMPLE VAC FOR RF POSITIONING, PULSE FOOT PEDAL FOR VACUUM, PRESS VAC |
| READY | RF | VAC |

1248

| CUTTER CLOSE FAILED |
|---|
| TO CLOSE BIOPSY AREA, PRESS SAMPLE TO CLOSE QUICKLY, PRESS SAMPLE VAC FOR VACUUM, PRESS VAC |
| READY | VAC |

1250

| BIOPSY FAILED |
|---|
| TO CLOSE BIOPSY AREA, PRESS SAMPLE TO CLOSE QUICKLY, PRESS SAMPLE VAC FOR RF POSITIONING, PULSE FOOT PEDAL FOR VACUUM, PRESS VAC |
| READY | RF | VAC |

1252

| BIOPSY AREA PART OPEN |
|---|
| TO CLOSE BIOPSY AREA, PRESS SAMPLE TO CLOSE QUICKLY, PRESS SAMPLE VAC FOR RF POSITIONING, PULSE FOOT PEDAL FOR VACUUM, PRESS VAC |
| READY | RF | VAC |

1254

| BIOPSY AREA PART CLOSED |
|---|
| TO CONTINUE BIOPSY, PRESS SAMPLE FOR VACUUM, PRESS VAC |
| READY | VAC |

1256

| BIOPSY AREA OPEN |
|---|
| TO CLOSE BIOPSY AREA, PRESS SAMPLE TO CLOSE QUICKLY, PRESS SAMPLE VAC FOR RF POSITIONING, PULSE FOOT PEDAL FOR VACUUM, PRESS VAC |
| READY | RF | VAC |

1258

| BIOPSY AREA OPEN |
|---|
| TO CLOSE BIOPSY AREA, PRESS SAMPLE TO CLOSE QUICKLY, PRESS SAMPLE VAC FOR RF POSITIONING, PULSE FOOT PEDAL FOR VACUUM, PRESS VAC |
| READY | RF | VAC |

1260

| BIOPSY AREA OPEN |
|---|
| TO CLOSE BIOPSY AREA, PRESS SAMPLE TO CLOSE QUICKLY, PRESS SAMPLE VAC FOR RF POSITIONING, CONNECT GEN-R FOR VACUUM, PRESS VAC |
| READY | VAC |

1262

| BIOPSY FAILED |
|---|
| TO CLOSE BIOPSY AREA, PRESS SAMPLE TO CLOSE QUICKLY, PRESS SAMPLE VAC FOR RF POSITIONING, CONNECT GEN-R FOR VACUUM, PRESS VAC |
| READY | VAC |

1264

| BIOPSY AREA PART OPEN |
|---|
| TO CLOSE BIOPSY AREA, PRESS SAMPLE TO CLOSE QUICKLY, PRESS SAMPLE VAC FOR RF POSITIONING, CONNECT GEN-R FOR VACUUM, PRESS VAC |
| READY | VAC |

1266

| TRIM AREA OPEN |
|---|
| TO CLOSE TRIM AREA, PRESS SAMPLE FOR VACUUM, PRESS VAC |
| READY | VAC |

FIG. 10C

UNIVERSAL MEDICAL DEVICE CONTROL CONSOLE

REFERENCE TO RELATED APPLICATIONS

This application is a continuation of U.S. patent application Ser. No. 11/980,956, now U.S. Pat. No. 8,652,121, which is a divisional of U.S. patent application Ser. No. 10/847,699, filed May 17, 2004, which is related to, and hereby claims the benefit of U.S. provisional application No. 60/475,747, filed on Jun. 3, 2003, each of which is herein incorporated by reference in its entirety and from which priority is claimed.

BACKGROUND

The present invention relates generally to medical devices, and more particularly to a universal control console for operating with a variety of medical devices. Still more particularly, the present disclosure relates to the design of a universal medical equipment control console that interfaces with a variety of handheld medical instruments, and the method to control the same.

Conventional medical equipment design typically requires separate, dedicated hardware and software control modules for each handheld medical device. Each of these devices requires a graphical display, microprocessor, interface circuitry and software to operate the medical device, and to provide the operator with pertinent status/action information. An "operator" is defined as any medical personnel capable of operating the medical device. The operator may be a nurse, a medical doctor, or a medical assistant.

The graphical user interface (GUI) will vary from device to device, thereby resulting in additional cost for operator training, proficiency, and certification. As the number of dedicated control modules increases, surgical and storage spaces must necessarily increase, as must the complexity of inventory logistics.

What is needed is a universal control console that can control a variety of medical devices, thereby eliminating the need for separate, dedicated control hardware for each medical device.

SUMMARY

In view of the foregoing, a universal medical equipment control console is provided that interfaces with a variety of medical devices.

This disclosure will provide a detailed description of how a medical device interacts with the universal medical equipment control console. Additional medical devices may be implemented. This concept allows for a universal control console with all the necessary hardware interface modules and software modules that can control a variety of medical devices, thereby eliminating the need for separate, dedicated control hardware for each medical device.

This universal control console will provide a graphical user interface (GUI) for all devices that would decrease the need for operator training and certification requirements while increasing the simplicity of operation. Additional benefits include reduced surgical space, storage space, and inventory logistics costs. Some advanced models of the universal control console may have the ability to handle multiple devices simultaneously.

In one example, a control console is disclosed for controlling one or more medical devices. The control console communicates to at least one medical device and, if needed, at least one peripheral device module associated with the medical device. The control console is microprocessor based for directing an operation of the connected medical device.

The construction and method of operation of the invention, however, together with additional objects and advantages thereof will be best understood from the following description of specific embodiments when read in connection with the accompanying drawings.

BRIEF DESCRIPTION OF THE DRAWINGS

FIGS. 10B to 10D present various display screens in relation to the states in FIG. 10A in accordance with one example of the present invention.

DESCRIPTION

Figure 1A:
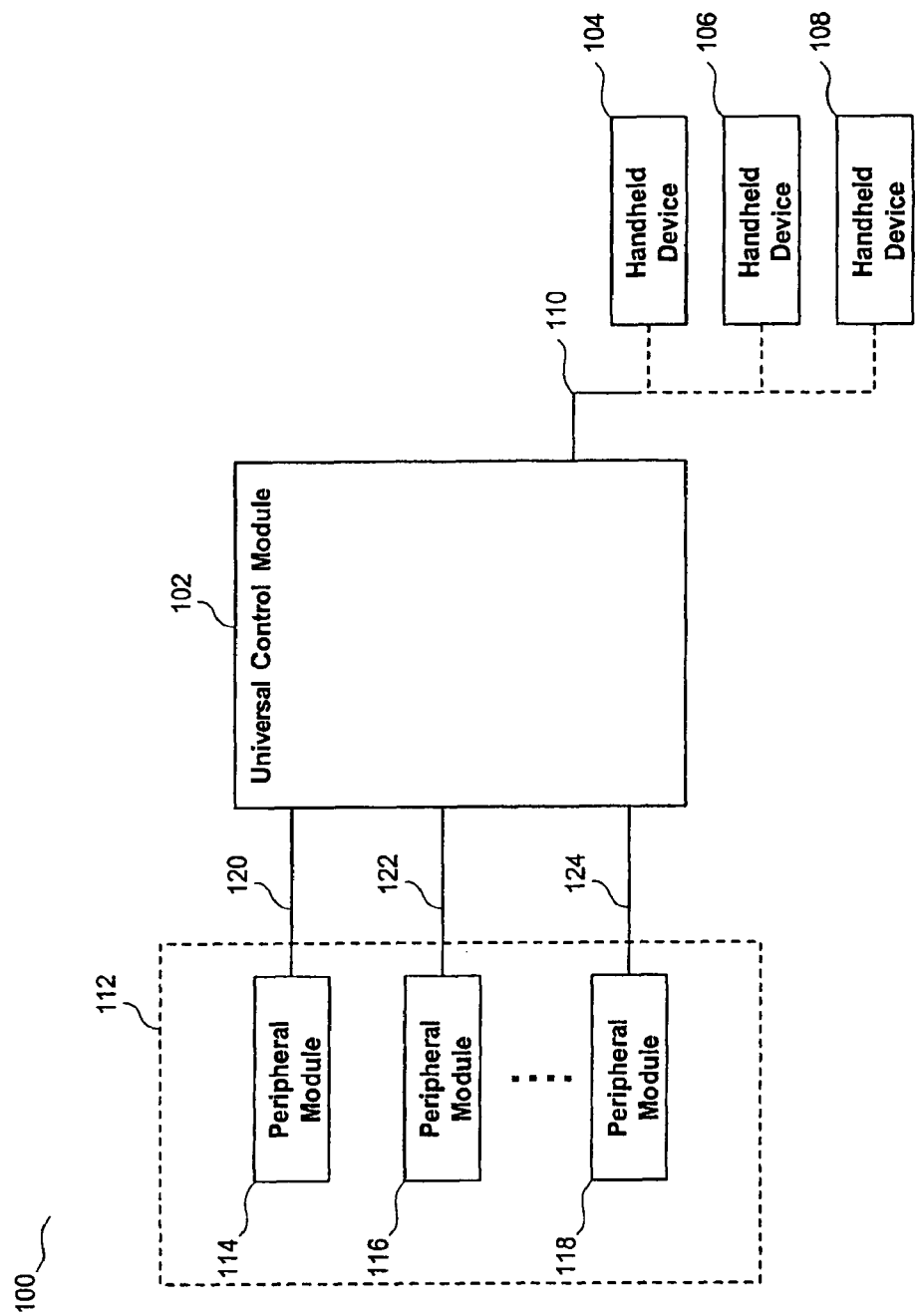
FIG. 1A is a schematic diagram illustrating a universal control console which embodies features of the invention operating with a plurality of medical devices.

FIG. 1A presents a diagram 100 illustrating the relationship between the universal control console 102 and a plurality of medical devices 104, 106 or 108 in accordance with one example of the present disclosure. Devices 104, 106 and 108 represent some of the many individual medical devices that may connect or communicate to the universal control console 102 via a connector 110 or via wireless communication links. Many of the medical devices are controllable by a computer based operating tool so that the universal control console can communicate and control the medical device in many ways without human interaction. In the following illustration, wherever it is said that a device or module is connected to another device or module, it is understood that the term "connected" may also mean that they can be connected wirelessly without physically connected through wires. In most of the time, at least one device will be connected to and operational with the universal control console 102. The universal control console 102 may also have a bypass mode in which a medical device may not be connected. The universal control console 102 may interface with and control the functions of any one of the devices 104, 106 and 108 via the connector 110.

In one embodiment, each of the devices 104, 106, and 108 may represent a biopsy probe, temperature probe, heart rate monitor device, drug infusion tools, anesthesia tools, or other surgical or medical device that may operate with the universal control console 102. These devices may serve various surgical or non-surgical functions such as separating specimen from tissue bed, encapsulating the separated specimen, insulating a cutter from body, fixing one end of a cutter while moving another end thereof. These devices may be made by or operated with products of SenoRx of Aliso Viejo, Calif. such as the SenoCor Biopsy Device and the EnCor Biopsy Device. The surgical devices may be energized mechanically or through radio frequency (RF) energy for performing the surgery. For instance, a RF surgical tool uses RF energy to remove unwanted body parts while the same function may be achieved by a mechanical tool such as a blade. Each of these medical devices may require a unique set 112 of peripheral modules 114, 116 and 118, which are connectable to and controlled by the universal control console 102 via connectors 120, 122 and 124, respectively. As an example, the device 104 may be a biopsy probe, which in turn may require a plurality of peripheral modules 114, 116 and 118, which further in turn may be an electro surgical generation (ESG) module, an illumination device, a footswitch module, and a vacuum/fluid pump module. It is understood that peripheral modules provides additional features or functions for the operation of the medical device, and can be of different forms and functions, and they may not be required to be physically connected to the universal control console as long as they can communicate therewith. In some cases, the peripheral devices are controlled by the medical device through the universal control console.

The universal control console 102 is a microprocessor-based electrical device with built-in software functions necessary to operate various medical devices. Each medical device contains a software script, stored in a memory device within the medical device for operating that particular device when connected to the universal control console 102. For example, the said software script may be stored in non-volatile memories such as erasable programmable read only memories (EPROMs), electrically erasable programmable read only memories (EEPROMs) or flash memories. When a medical device is connected to the universal control console 102, this software script will be downloaded into the universal control console random access memory (RAM). This software script will enable the universal control console 102 to control the functionalities of the particular medical device and to display its pertinent information. During the operation of a medical device, the Graphical User Interface (GUI) software will display information relevant to the operation of the universal control console 102 and the medical device to the operator. It is understood by those skilled in the art that the information displayed may vary depending upon the type of medical device connected, the operational state of the medical device as well as other environmental factors affecting the operation of both the medical device and the universal control console 102.

It is understood that although traditionally the medical devices are connected to the universal control console 102 through wired connections (including connectors and wires) or battery powered for their operations, the control of the medical devices by the universal control console 102 can be easily implemented through wireless communications. Needless to say, certain peripheral devices may have to be physically connected to the medical device to deliver fluid or assert vacuum. The conventional wired connections have certain advantages such as low signal interferences, but the wireless technology can turn the operation of the medical device to mobile operation, which benefits the operator as well. For example, other than the power output provided by the universal control console 102, almost all the control signals can be sent through a predetermined wireless communication channel using technologies such as Bluetooth or 802.11 compliant wireless technologies. When the medical device is battery powered, then the operation may be all mobile. It is also practical that the wired communication channels may be used together with the wireless communication channels so that the universal control console can take advantage of the available wireless technologies for providing convenience to the operator, while still benefiting from using some conventional wired technologies. Similarly, analog signals used in the communications can be replaced by digital signals if appropriate since the digital signal processing technology has also advanced. In short, while the present disclosure only provides some examples for illustrating the inventions, it should be understood that communications between devices can take various forms and the universal control console 102 is designed to use the most practical technologies for fulfilling the need of the operators.

Figure 1B:
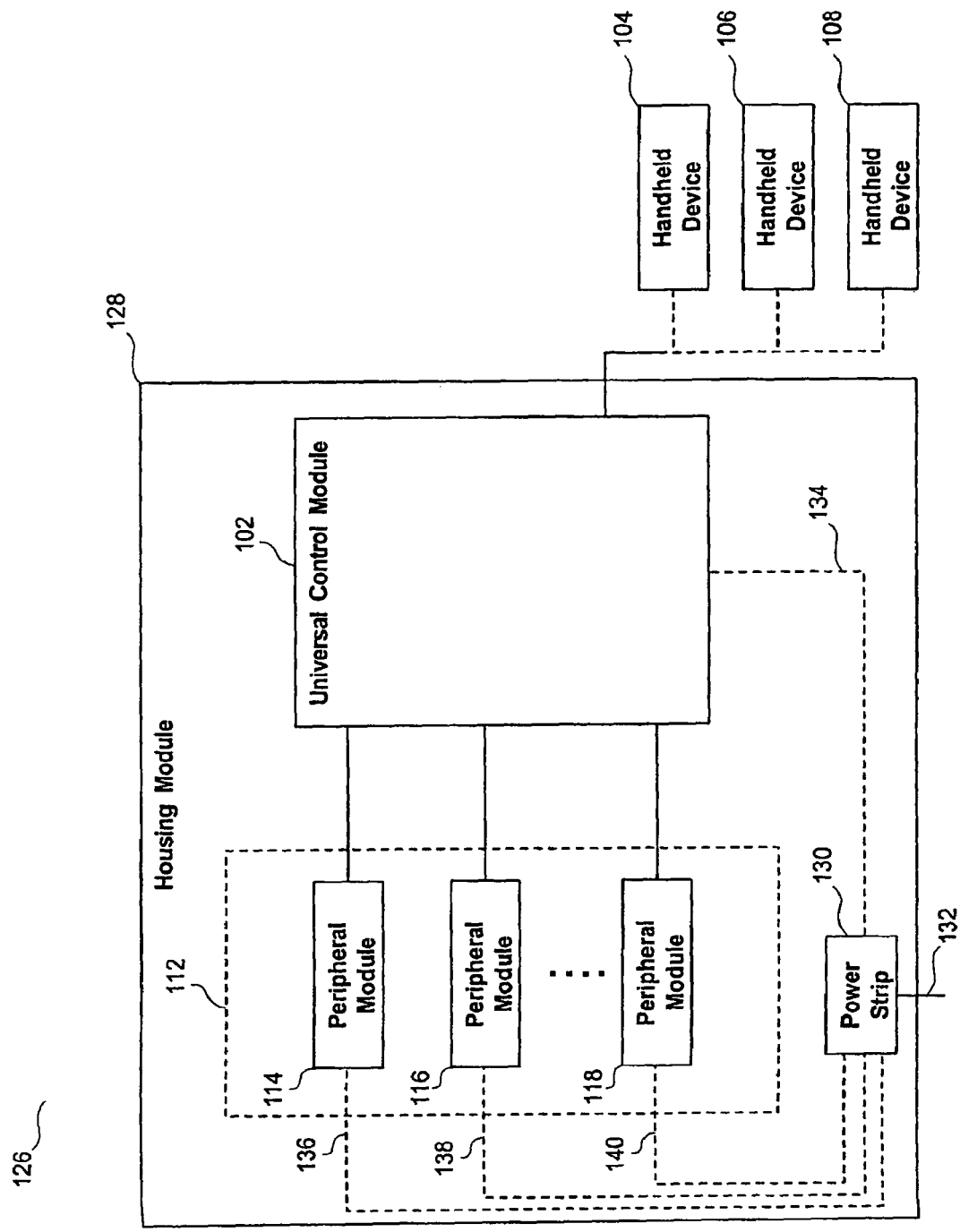
FIG. 1B is a schematic diagram illustrating a universal control console which embodies features of the invention operating with a plurality of medical devices and peripheral modules through a housing module.

A housing module may also be provided to house, and to supply electrical power to, some of the aforesaid modules and equipments. An example is provided in FIG. 1B, which is a schematic diagram 126 illustrating the relationship among a housing module 128, the universal control module 102 and the unique set 112 of peripheral modules 114, 116 and 118. The housing module 128 includes a power strip 130, which connects, via a power cord 132, to an electrical power source, such as a 220-240V AC power source. The power strip 130 is utilized to distribute electrical power to a plurality of modules and equipments. A line cord 134 may be utilized to deliver electrical power from the power strip 130 to the universal control module 102. A plurality of line cords 136, 138 and 140 may also be utilized to deliver electrical power from the power strip 130 to the peripheral modules 114, 116 and 118, respectively. It is understood that the housing module 128 may provide docking stations (not shown) for the handheld medical devices 104, 106 and 108. It is further understood that the housing module 128 can be a cart or a portable cabinet; that the power strip 130 and the aforesaid modules are fixed-mounted or screw-mounted onto the housing module 128; that the housing module 128 includes a plurality of moving wheels and accessible handles; and that the housing module 128 includes a wire latch that organizes and secures a plurality of line cords and data cables. Essentially, the housing module 128 functions as an organizer, a power distributor and an ergonomic solution for the operator to access the plurality of modules and equipments.

Figure 2:
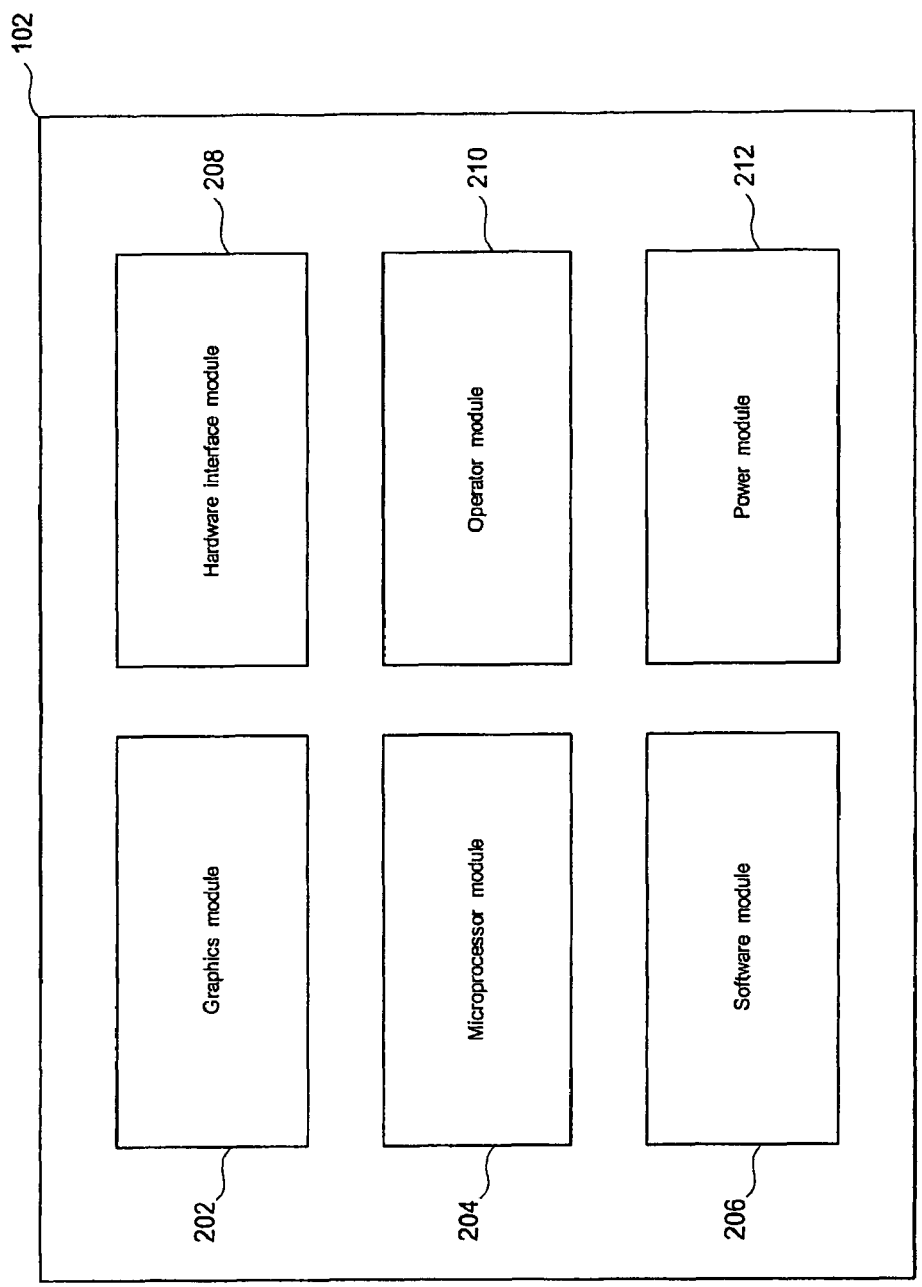
FIG. 2 illustrates the major components of the universal control console shown in FIG. 1A or 1B.

FIG. 2 illustrates several components of the universal control console 102. The universal control console 102 includes a graphics module 202, a microprocessor module 204, a software module 206, a hardware interface module 208, an operator module 210 and a power module 212.

The graphics module 202 may include a cathode ray tube (CRT) display, a liquid crystal display (LCD) or any other type of display that may be used to display information relevant to the operation of the universal control console 102 and medical devices. The graphics module 202 may also require a piece of Graphical User Interface (GUI) software that is used to display all pertinent information to the operator.

The microprocessor module 204 may include microprocessors, motherboard circuitries, memories and other functional electronic devices that enable the universal control console 102, the operator controls thereof, the functions of medical device, and the functions of peripheral modules. It may also interface with an external computer via an external computer interface connector for system troubleshooting, software upgrade, and other shop functions.

The software module 206 controls the logical and interface functions of the universal control console 102, the logical and interface functions of the medical devices attached thereto, the logical and interface functions of the peripheral modules attached thereto, and the operator control switches therein. The software module 206 may also generate various control signals such as audible tones (for example, sounds of Bong, Click, and Alarm) that are applied to a speaker located within the universal control console 102. The Bong and Click tones may be adjustable by a predetermined setting. Depending on software specification, the alarm tone may or may not be adjustable. As an example, the software may be written in "C" code, although it is understood by those skilled in the art that various other software languages may be used to write the software for the universal control console 102. Specifically, the software module 206 may include any combination of the following: core software operating the universal control console 102, GUI software for presenting graphics in the graphics module 202, built-in self-test (BIST) software, and software for controlling and interfacing with medical devices and peripheral modules. Each medical device, when connected to the universal control console 102, may download a software script. This software script will allow for the control of the particular medical device functions and display its pertinent information.

The hardware interface module 208 may include circuitries and connecting modules necessary to allow medical devices or peripheral modules to be connected to the universal control console 102. These connecting modules may be general connectors compliant with various well-known standards, including but not limited to Institute of Electrical and Electronics Engineers (IEEE) standards and International Organization of Standardization (ISO) standards. These connectors may also be proprietary connectors specific to a particular medical device or peripheral modules, or a particular line of medical devices or peripheral modules. In addition, the connecting modules may be a circuitry for communicating wirelessly with a device controlled by the universal control console.

For example, the hardware interface module 208 may have a computer interface connector. The computer interface connector is used for system troubleshooting, software upgrades, and other shop functions. This connector contains connectors for RS-232 communication, connectors for background debug mode (BDM), and connectors for other shop activities. In another example, the hardware interface module 208 may have an AC power input connector, which may be a three-wire connector connectable to 100-120 VAC and/or 220-240 VAC, at 50-60 Hz. In yet another example, the hardware interface module 208 may have an AC power output connector, which is connectable to other peripheral equipments and which provides the other equipments with AC power. In yet another example, the hardware interface module 208 may have a DC power output connector, which is connectable to other peripheral equipments and which provides the other equipments with DC power. It is understood that either DC or AC power can be delivered to an illumination device such as a light bulb or any surgical lighting device attached to or integrated with a medical device such as a biopsy probe used with the control console. The control console may provide further remote operation control for the illumination device.

Other hardware interface circuitry and connectors implemented into the universal control console 102 may depend upon the medical devices and its associated peripheral equipment that have been certified to operate with the universal control console 102. As additional medical devices are selected, upgrades to the hardware and software may be required. Since analog and digital signals may co-exist in various operations, the universal control console may have analog-to-digital (A/D) converters or even digital-to-analog (D/A) converters contained therein for processing various signals coming in or going out from the universal control console.

Referring back to the previous embodying example, the biopsy probe may require an ESG module, a footswitch module, and a vacuum pump module. The biopsy probe and its associated peripheral modules in turn may require the following interface connectors: a medical device connector, an ESG connector, a footswitch connector, and a vacuum pump connector.

The medical device connector may contain a plurality of copper wires for bi-directional digital communications, EEPROM communication, encoder functions, light emitting diode (LED) & relay control, motor control, power, and ground. The ESG connector may provide bi-directional communication for the control and status of the ESG module and the universal control console 102, and may include a RS-485 data bus for status communication. The footswitch connector may pass information from the footswitch module to the universal control console 102, thereby allowing the operator to control the ESG module and the universal control console 102 by the tapping of the foot. Finally, the vacuum pump connector may provide data and control information between the vacuum system and universal control console 102. It may contain system data and clock lines, vacuum level and control lines, and status lines.

The operator module 210 may include various pushbutton switches and indicators that assist the operator to operate the universal control console 102. For example, there may be, adjacent to the display screen, three operator pushbutton switches that are under software control. The function of the switches may be dependent upon the display screen at a particular instance. The display screen displays the required actions and what action may be activated with a particular switch at a given instance.

To further illustrate how the operator module 210 assists the operator, the operator module 210 may have two indicator lights, one of which is an orange standby indicator light on the front panel that may be activated when the rear mounted power switch is depressed and the system enters a standby state, while the other of which is a green indicator light on the front panel that may be activated when a front mounted power switch is depressed for a minimum of 2 seconds, thereby signaling the universal control console 102 to kick-start its boot up sequence. When the front mounted power switch is depressed again for a minimum of 2 seconds, the display may indicate that the universal control console 102 is in the process of shutting down. During an orderly shutdown, the universal control console 102 may complete any actions required by the medical device, save any required settings, and then return to the standby mode.

The power module 212 may include a transformer, AC power input and output connectors, a power system, fuse, and a power switch. The power module 212 may supply power to the rest of the universal control console 102, and may supply power to other peripheral modules and medical devices attached thereto.

Figure 3:
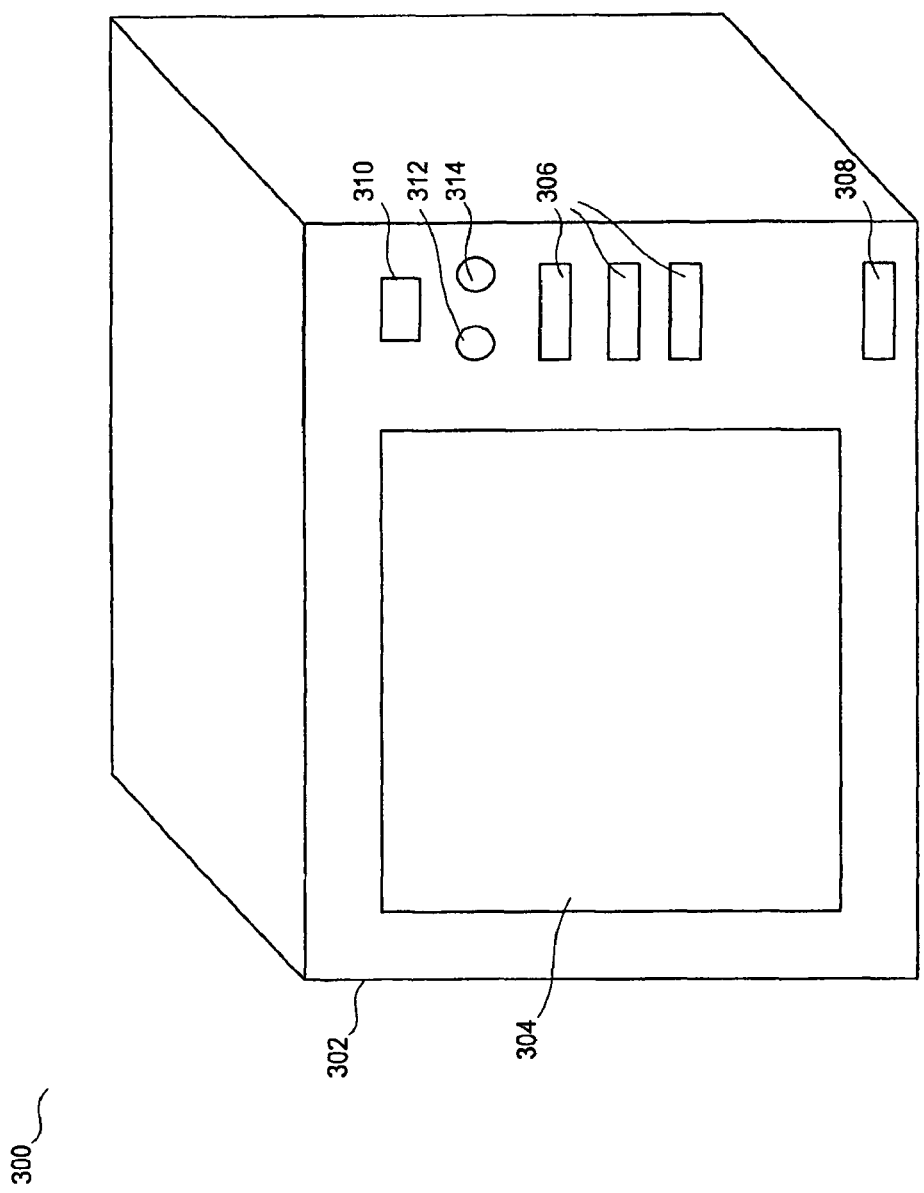
FIG. 3 illustrates a frontal view of the universal control console shown in FIG. 1A embodying features of the invention.

FIG. 3 illustrates a frontal and top view 300 of the universal control console 102 embodying features of the present invention. The front of the case enclosure 302 includes a graphical display screen 304, various operator control switches 306, a medical device connector 308, a front power switch 310, an orange "standby" indicator light 312, and the green "on" light 314. It is understood that the connector 308 is an example for a connecting module which either physically connects to a device or wirelessly communicates to a device without any physical connection existing therebetween.

Figure 4:
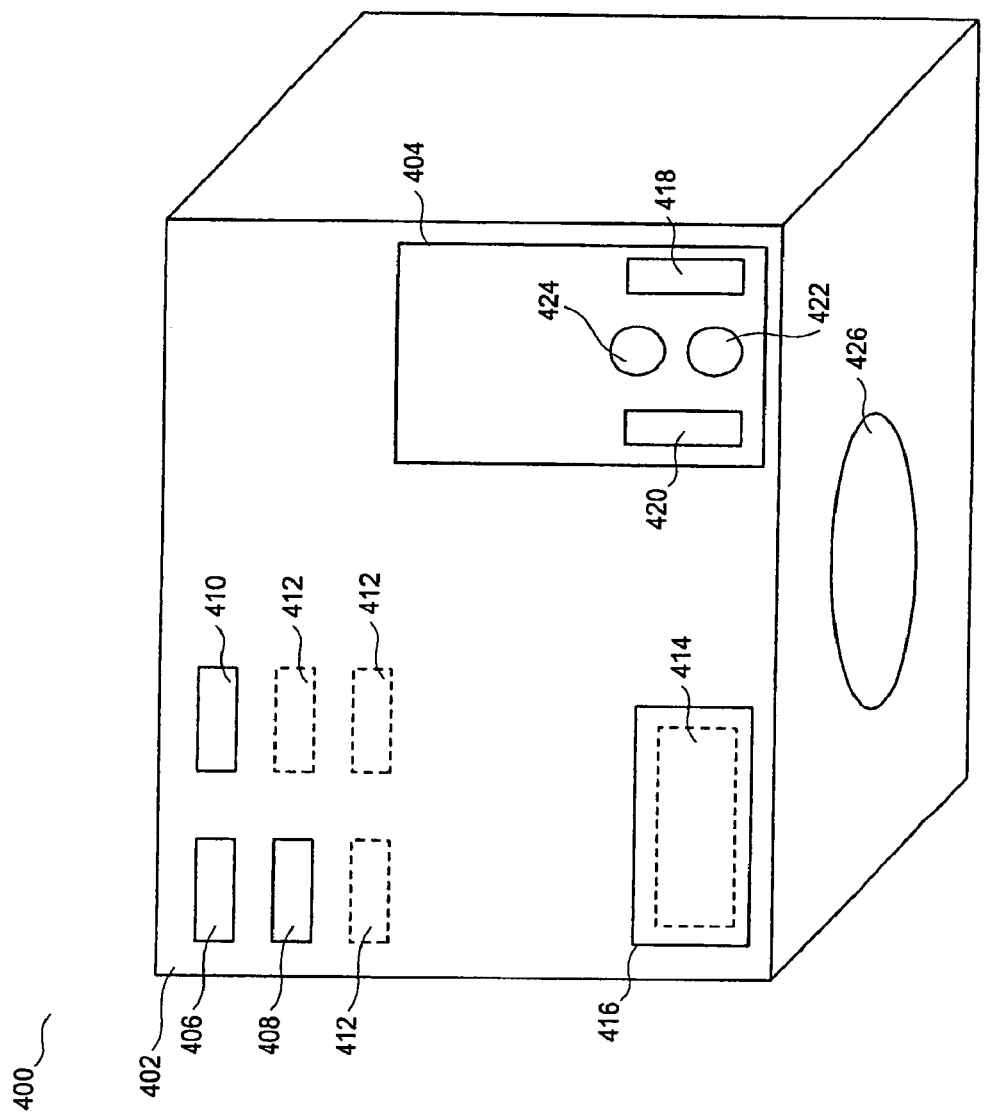
FIG. 4 illustrates a rear view of the universal control console shown in FIG. 1A embodying features of the invention.

FIG. 4 illustrates a rear and bottom view 400 of the universal control console 102 shown in FIG. 3. The rear of the case enclosure 402 includes a power module 404, a footswitch connector 406, a vacuum connector 408, an ESG connector 410, spare connectors 412 for future medical device/peripheral equipment additions, and the external computer interface connector 414 behind the removable panel 416. The power module 404 includes the input power connector 418, output power connector 420, AC power fuse 422, and the rear power switch 424. The bottom of the enclosure 402 includes the alarm speaker 426 for the Bong, Click, and Alarm tones.

Figure 5:
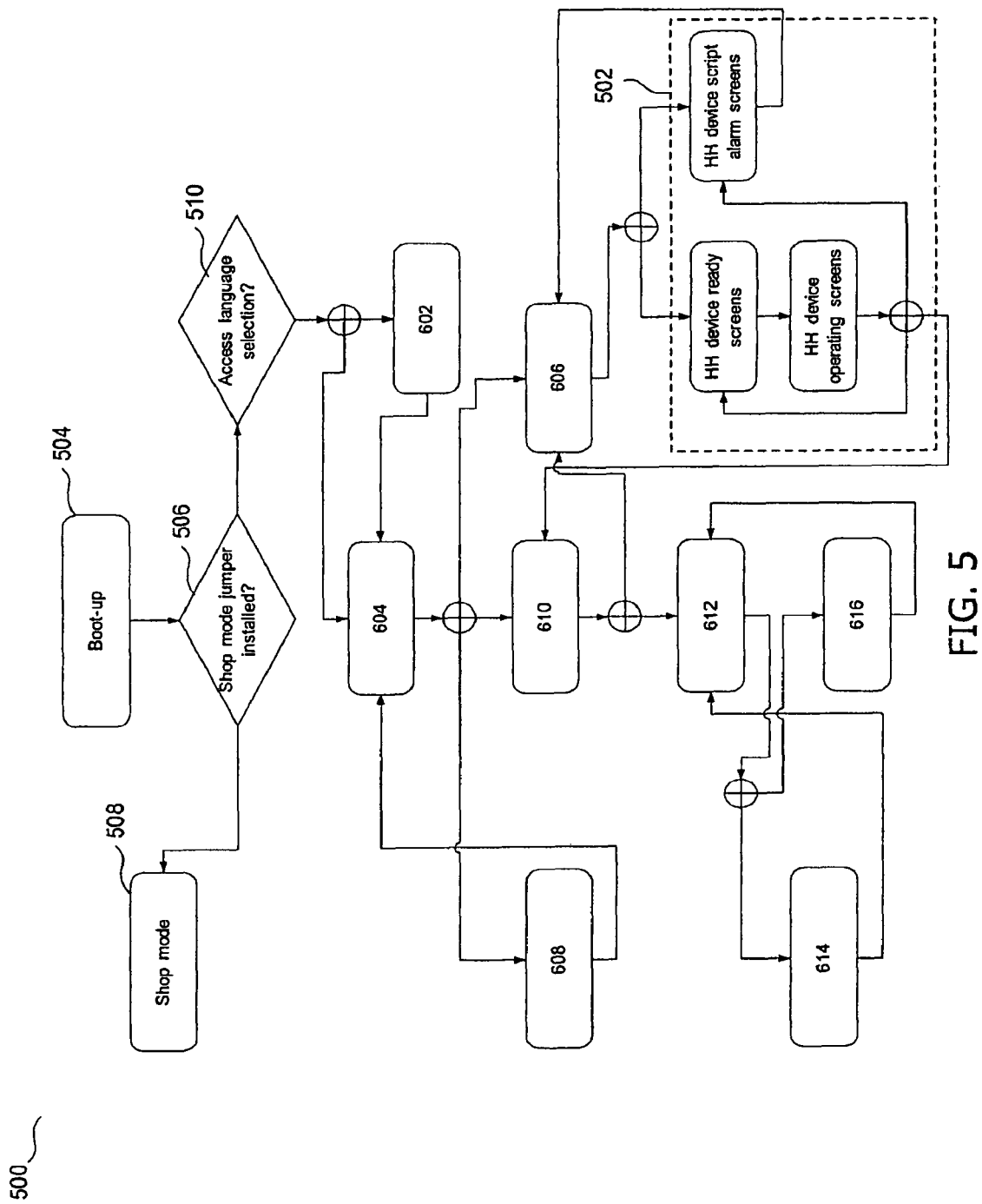
FIG. 5 presents a flowchart illustrating the relationship between various Graphical User Interface (GUI) display screens embodying features of the invention.
Figure 6:
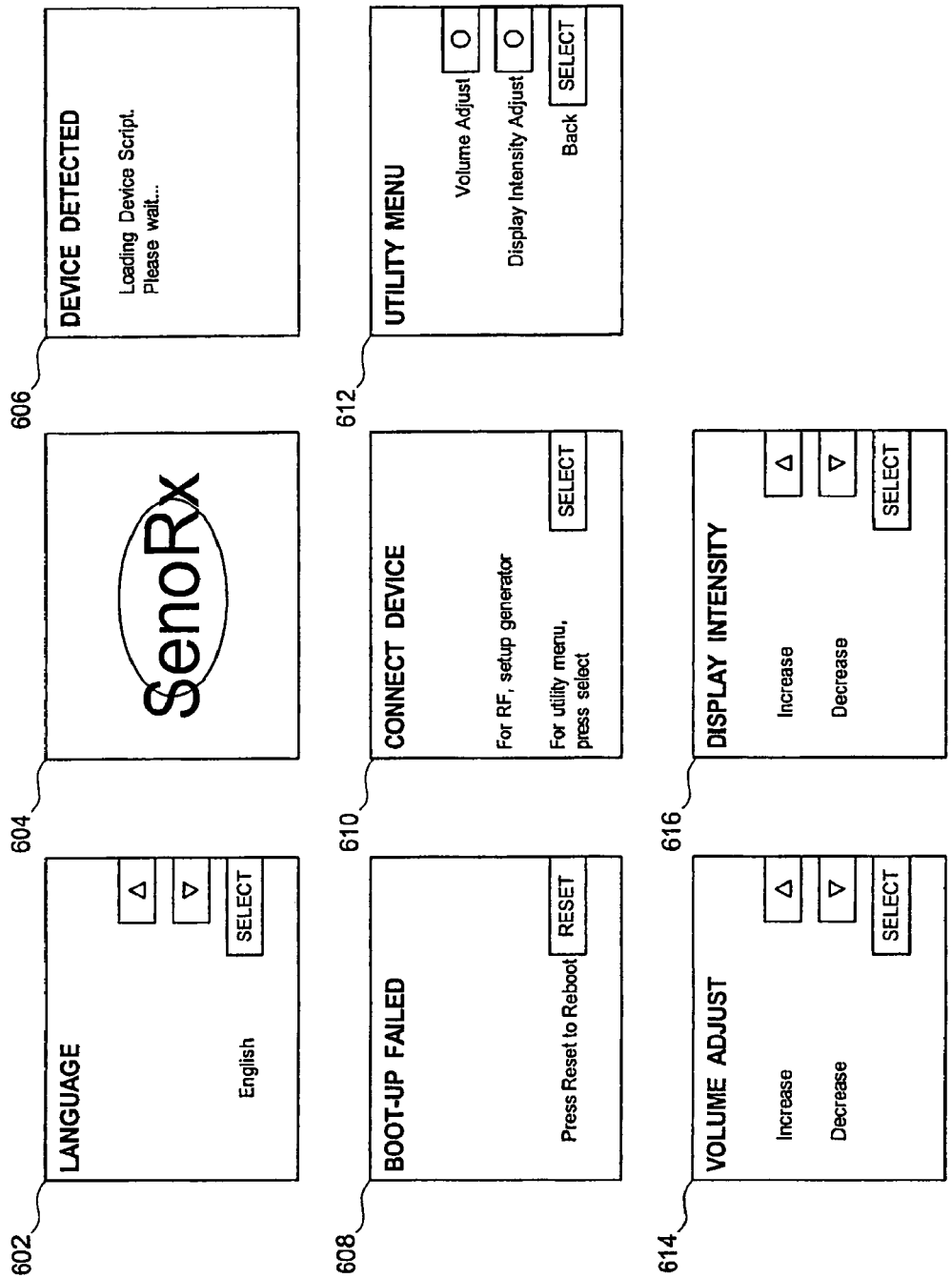
FIG. 6 represents various display screens for the universal control console embodying features of the invention.

FIG. 5 presents a flowchart 500 illustrating the relationship between various display screens, which are referred to and shown in FIG. 6, in accordance with one example of the present disclosure.

In particular, the flowchart 500 illustrates the software flowchart covering the initial boot-up, medical device connection, utility mode setup, boot-up alarm sequence and the downloading of the medical device script. A general high-level software flow 502 illustrates how the software module generally handles any medical device that is connected to the universal control console 102. This software flow may be unique for each medical device operation.

The flowchart 500 begins at a boot-up process 504 that occurs when the power-on sequence is started. In decision box 506, the universal control console 102 checks the shop mode jumper to determine if the system should go into the shop mode for troubleshooting/upgrade, as illustrated by box 508, or continue the normal boot-up process. A decision box 510 determines whether a language selection screen should be displayed to the operator to select the desired operator language. If the language selection screen should be displayed, a language screen, which may look like the screen 602, may be displayed. This selection is accomplished through the use of the pushbutton switches located adjacent to the graphical display screen. The universal control console software script controls the functions of these switches. Once the desired language is selected, a boot-up splash screen that may look like the screen 604 is displayed.

If the medical device has been connected, the script will go directly to download the medical device script, and a screen that may look like the screen 606 is displayed to the operator. If an alarm is generated during the boot-up process, the script will transfer to the boot-up alarm screen 608 to ask the operator to reset the system. If no medical device has been connected, a bypass mode screen that may look like the screen 610 may be displayed, wherein the operator is asked to connect the medical device or to access the utility menu. If the operator connects the medical device, then the script goes directly to the device script download mode and the screen 606 may be displayed. If the operator wishes to enter the utility mode, then the operator depresses the "SELECT" pushbutton switch; thereby switching to the utility screen, which may look like the screen 612. The utility menu allows the operator to adjust the volume level, which may be accomplished in a volume level screen that may look like the screen 614, to adjust the display screen intensity level, which may be accomplished in a display screen intensity level screen that may look like the screen 616, or to go back to the screen 610 such that the operator may connect the medical device. Once the correct volume or display screen intensity is selected, the operator is transferred back to the bypass mode screen. When the medical device is connected to the universal control console 102, the script goes directly to the device script download mode and screen 606 may be displayed. Once the script is downloaded, the downloaded script controls the universal control console 102 and its display as determined by the type of medical device connected. In flow 502, the connected medical device determines the system operation and display screens. One example of the system operation and display screens in flow 502 are presented, in detail, in FIGS. 10 to 17. Through this flow, the appropriate control configuration of a medical device is managed by the universal control console 102. For example, it detects and configures itself to match the operating configuration of the medical device. For example, it detects and provides an appropriate voltage supply for operating the medical device. It may also provide control signals to control the motor in the medical device. It may provide appropriate GUI windows to the operator with regard to the medical device so that the operator only needs to deal with relevant GUI windows for operating the medical device. If a vacuum pump is needed to be used in conjunction with the medical device, it not only will indicate to the operator whether a vacuum pump is properly connected, it will also provide the appropriate operating voltage to the vacuum pump. In short, the universal control console 102 is to assist the operator to operate multiple medical devices with ease. To the extent possible, all configurable items for operating the medical device are either automatically provided to the device or prompted to the operator to be chosen so that they can be then provided to the connected device.

The three pushbutton switches are utilized in the displays that require an operator action, such as language selection, volume adjust, reset, etc. It is understood by those skilled in the art that all display screens in FIG. 6 are presented to illustrate the spirit of the invention, are subject to change, and are not considered to be the only version.

Figure 7:
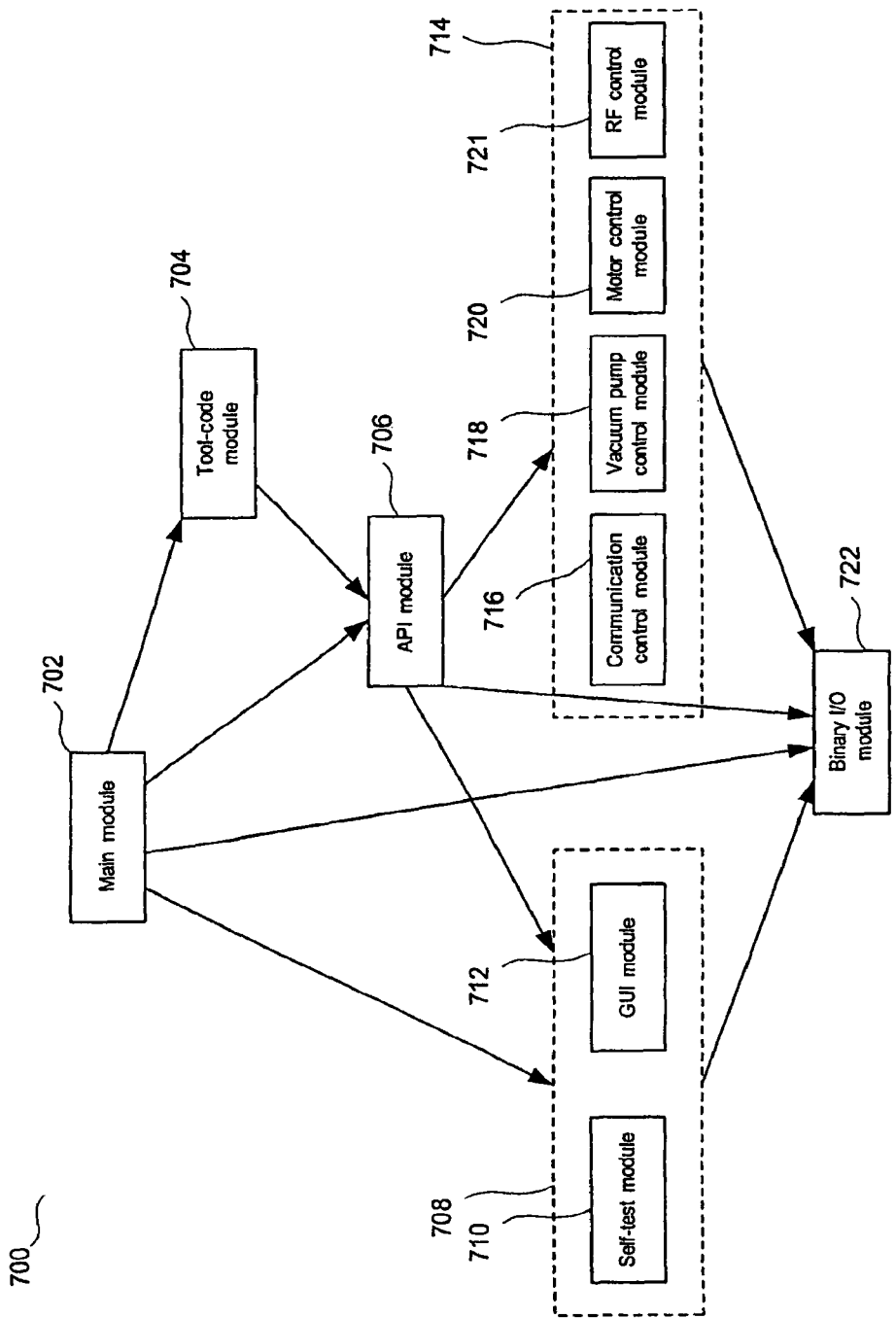
FIG. 7 illustrates a flowchart illustrating an interactivity between various software components of the universal control console embodying features of the invention.

FIG. 7 presents a flowchart 700 illustrating the high level interactivity between various software components of the universal control console 102 in accordance with one example of the present disclosure. The components include a main module 702, a tool-code module 704, an application program interface (API) module 706, a core software module 708 that in turn includes a self-test module 710 and a GUI module 712, a control software module 714 that in turn includes a communication control module 716, a vacuum pump control module 718 and a motor control module 720, a RF control module 721, and a binary I/O module 722.

The main module 702 contains software functions for the operation. For example, it includes a reset function in assembly code that is required to start the controller and run a portion of the self-test. The main module 702 also includes a high-level code that runs the main loop and performs some additional self-tests, including memory and processor tests.

The tool-code module 704 loads the tool code from nonvolatile memories into the code buffer of the volatile memories and then runs tests thereon. The tool code may be tested by a variety of methods. For example, one tool code testing method is by using cyclic redundancy check (CRC). The tool-code module 704 may also allow the universal control console 102 to write to nonvolatile memories.

Another functionality of the tool-code module 704 may include the testing of nonvolatile memories. In other words, the tool-code module 704 may run periodic tests to ensure that nonvolatile memories are not corrupted.

The API module 706 may include an API called by the tool code, and an API manager that is used to manage the said API. The API is used by the tool-code module 704 to request the universal control console 102 to act in a certain manner. As an example, one implementation strategy may call for the use of software interrupts to request certain API routines, via the API module 706.

The self-test module 710 may include built-in, self-test (BIST) software that is used to perform various self-testing operations. Most of these self-testing operations should be non-invasive, i.e., they should test for mis-configuration, but should not actively induce one.

The GUI module 712 may include software that is used to draw outputs to the screen. This GUI module 712 may also include functions such as the initialization of the color palette upon boot-up, the drawing of the first splash display screen, and the refreshing of subsequent display screens.

The communication control module 716 may include software that controls the inputs and outputs through the RS-485 connector. The communication control module 716 keeps all information about a port in a table, which is typically indexed to ensure fast referencing. The interrupt callback routines of the communication control module 716 may be passed to a hardware access layer, thereby enabling the universal control console 102 to receive incoming data.

The vacuum pump control module 718 may include software that controls the vacuum pump system interface. For example, the vacuum pump control module 718 may be able to detect vacuum and pump power. It may also be able to translate commands sent by the universal control console 102 to actual pressure, and vice versa.

The motor control module 720 may include software that controls the motors located in the medical device. The motor control module 720 may provide the universal control console 102 with various operating modes. For example, the motor control module 720 may provide a feedback-controlled operating mode, which may employ a variety of discrete proportional-integral-derivative (PID) feedback algorithms to provide feedback functionality. The motor control module 720 may also provide various constant operating modes, including constant current and constant voltage operating modes, which may be necessary for medical devices that require a steady motor. The RF control module 721 is dedicated to control devices using RF energy.

The binary I/O module 722 may include software that performs the binary input and output. For example, the binary I/O module 722 maps an array of binary outputs to its corresponding array of hardware address registers, and writes data flags to the latter. For example, when the "power-off" button is pressed, the binary I/O module 722 first searches for and locates the corresponding hardware address register, and then begins a power-off sequence. In another example, when a motor is stopped, the binary I/O module 722 may read the corresponding hardware address and return a flag indicating that the particular motor has been stopped.

The universal control console embodying features of the present invention may be operated in regular ambient temperature and usually requires no special sterilization. The operating voltage may be from 100 to 240 VAC with corresponding standard current limits. It also meets other industry required environmental conditions such as the CISPR 11 or IEC 60601-1-2:2001 for electromagnetic generation and IEC601-2-2 Section 44.3 for drip, splash and immersion requirement. It also meets various international standards including various safety requirements for medical equipments in different countries such as Japan, Canada, EU, and US.

Figure 8:
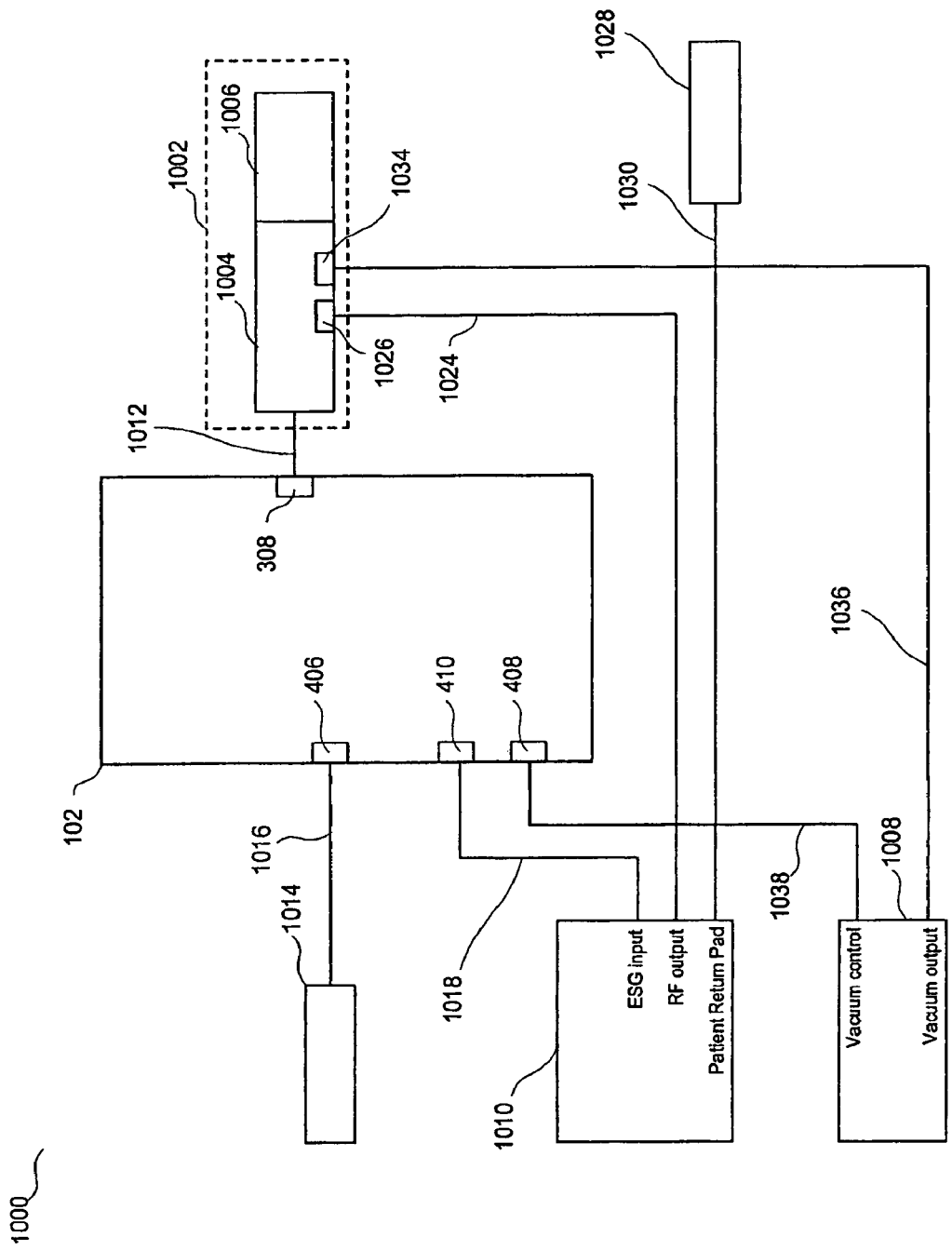
FIG. 8 illustrates a design embodying the interaction between a biopsy device and the universal control console.
Figure 9:
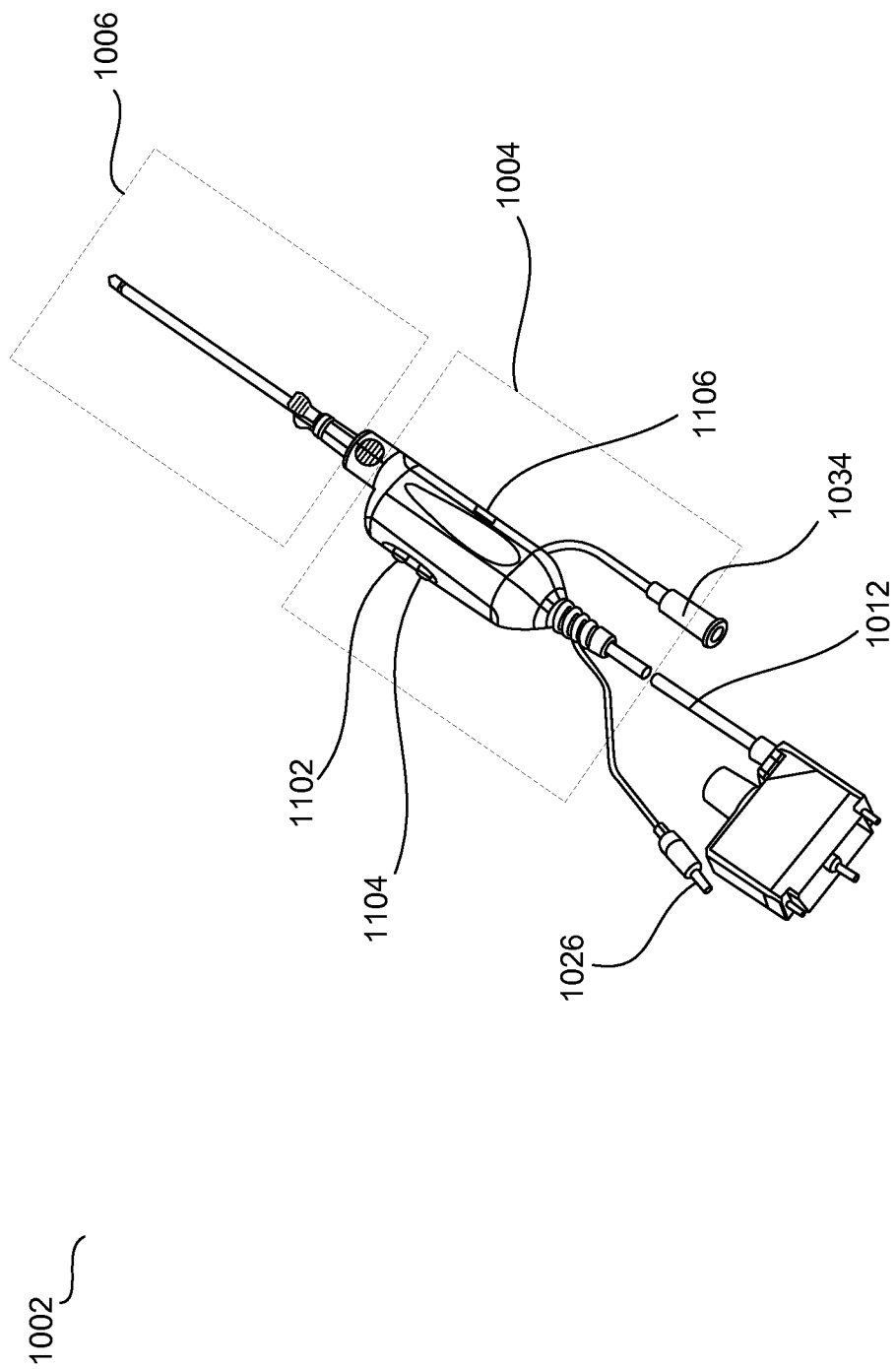
FIG. 9 illustrates the biopsy device.

FIG. 8 illustrates a design 1000 embodying the interaction between a biopsy device 1002, as further illustrated in FIG. 9, and the universal control console 102 in accordance with one example of the present disclosure.

General Design Specifications

In this embodying design 1000, the medical device such as a biopsy device 1002 consists of the SenoCor DR3000 biopsy driver 1004 and a surgical element such as the SenoCor 360 biopsy probe 1006. The biopsy probe 1006 and biopsy driver 1004, when used in conjunction with the universal control console 102, a VS3000 vacuum system 1008 and a SenoRx ES300 ESG module 1010, are designed to obtain breast tissue biopsy samples. The specifications of SenoCor DR3000, SenoCor 360, VS3000 and SenoRx ES300 may be found at SenoRx's website, at:
http://www.sensorx.com/products/product_catalog/index-.asp With reference to FIGS. 3, 4 and 8, the universal control console 102 is connected from the medical device connector 308, via a control cable 1012, to the biopsy driver 1004. When the biopsy device 1002 is connected as shown in FIG. 8, the universal control console 102 may provide user interface, motor speed control, and operator feedback for the biopsy driver 1004.

Design Features

The embodying design 1000 provides many features, four of which are highlighted below:

1) Radiofrequency (RF) Cutting Tip

The biopsy probe 1006 that attaches to the biopsy driver 1004 incorporates a disposable RF cutting tip. The RF cutting tip enables the device to slide easily through difficult heterogeneous breast tissue, and to penetrate through dense lesions, thereby improving the targeting capability of the device. RF energy is developed by the ESG module 1010, which is controlled by a dual footswitch 1014 and the universal control console 102. The generator-enable signal is routed from the footswitch 1014 via a cable 1016 to the connector 406, and then through the ESG connector 410 via a cable 1018 to a footswitch input connector on the ESG module 1010. The cable 1018, which may be designed for RS-485 communication, provides a communication path to allow the universal control console 102 to configure the ESG module 1010 for the biopsy device 1002. The RF output from the ESG module 1010 is fed, via a RF cable 1024, to a RF cable connector 1026 of the biopsy driver 1004. The patient return pad 1028 is connected to the ESG module 1010 via a cable 1030.

2) Integrated Coaxial Probe

The disposable biopsy probe 1006 consists of an inner cutting trocar and sample chamber with an outer probe. A trocar is a sharply pointed surgical instrument fitted with a probe and used to insert the probe into a body cavity, typically, as a drainage outlet. An outer probe is typically a small tube for insertion into a body cavity. After a lesion has been targeted, the outer probe remains in place while the inner sample chamber is removed following the removal of a biopsy specimen. The above functions are generated by DC motors in the biopsy driver 1004 that provide linear or rotary motions for the disposable biopsy probe 1006. Medical devices may contain up to four DC motors and each motor is driven by a DAC output located in the universal control console 102. These signals and the other required signals are routed through the medical device connector 308 and the control cable 1012 to the biopsy driver 1004.

3) Circumferential Vacuum Assisted Biopsy System

The device 1002 harvests tissue from a full 360-degree radius, thereby enabling harvesting of tissue directly from the center of the suspicious mass. This process is assisted by the use of the vacuum switch located on the driver 1004 to remove any excess fluid from the biopsy area. Vacuum is applied by the vacuum system 1008 to a vacuum tube connector 1034 of the biopsy driver 1004 via a vacuum tube 1036. The vacuum system 1008 is under the control of the universal control console 102 via a cable 1038, which connects to the vacuum connector 408.

4) Control Buttons

With reference to FIG. 9, the biopsy device 1002 includes the biopsy driver 1004 and the biopsy probe 1006, and incorporates three easy to use push buttons: "sample", "vacuum", and "eject". To sample tissue, the operator pushes the "sample" button 1102. To remove excess fluid from the biopsy cavity, the operator pushes the "vacuum" button 1104. To change probes for the next operation, the operator pushes certain functional key or unlocking mechanism such as the "eject" button 1106, after which the disposable probe is easily removed. There are two optical sensors to determine probe size (e.g., diameter) and indicate to the system that the disposable probe is in place or removed. It is understood by those skilled in the art that the actions associated with the said buttons may differ in different probe designs, dependent upon functional and software control requirements.

Technical Specifications

Specifications for seven of many connectors, cables and tubes associated with the universal control console 102 are shown as follows:

1) The Medical Device Connector

With reference to FIGS. 3, 8 and 9, the connector 308 is a 56-pin connector, with shielded cable and with non-isolated I/O. The inputs from the medical device is preferred to have six digital wires (switches or position sensors) as well as eight encoder wires (two signals lines per encoder). The outputs to the medical device in this example contain four wires for power (+12 VDC, −12 VDC, +5 VDC, ground), six digital wires for LED indicators and relay controls, and eight wires for motor drive control (two wires per motor). The medical device is preferred to have up to 4 DC motors. For example, the universal control console 102 may provide 12-bit DAC outputs for each motor. There is a maximum of 2 Amps for all four motors. Each motor can draw up to 1 Amp, and maintain a 2 Amp-limit on all four motors. In addition, eight wires are used for EEPROM communication, two wires may be used for grounds (one for shield, the other for connector case), and five spare wires are included for future expansion. It is understood that various types of motors can be used by different medical devices, and the universal control console 102 can implement appropriate connectors for controlling the medical device with special requirement for the connector.

2) The Footswitch Connector

The connector 406 is a 12-pin connector, with shielded cable and with isolated I/O. The footswitch may use two wires for the active signals, one wire for the common return signal, one wire for a shielded signal and eight spare wires for future expansion.

The ESG connector 410. The connector 410 is a 15-pin connector, with shielded cable and with isolated I/O. The connector 410 may contain inputs and output to and from the ESG module 1010 for communicating its status or configuring the ESG module 1010 using a RS-485 communication bus. The connector 410 may also contain several spare wires for future expansion.

3) The Vacuum Connector

The connector 408 is an 18-pin connector, with shielded cable and with isolated I/O. The connector uses two wires for vacuum system data and clock. The inputs contain four bits for vacuum level plus two bits for control. Also included are wires that carry power-on and vacuum-ready status signals.

The external computer interface connector 414. The connector 414 is a 14-pin connector, with non-shielded cable and with non-isolated I/O. It contains 10 wires for BDM communication, three wires for RS-232 communication, and one wire for the shop mode switch that is in turn used for system troubleshooting and/or upgrade.

4) The Input Power Connector

The connector 418 is a 3-pin connector, with a non-shielded, removable cord. The input power may be 100/220 VAC, at 50 or 60 Hz, with a 2 Amps maximum input limit.

5) The Output Power Connector

The connector 420 is a 3-pin connector, with a non-shielded, removable cord. The output power may be 100/220 VAC, at 50 or 60 Hz.

6) Driver Components

The device 1002 has the following components that are controlled by the software script downloaded into the universal control console 102:

7) Stroke Motor

The stroke motor controls the axial motion of the cutting sleeve of the device 1002. The motor is in turn controlled by the motor control module 720.

8) Cutting Motor

The cutting motor controls the rotational motion of the cutting sleeve of the device 1002. The motor is in turn controlled by the motor control module 720.

9) Vacuum And Sample Switches

The vacuum and sample switches of the device 1002 are contact inputs to digital inputs of the control module 102. The script uses the API as specified in the API module 706 to retrieve the values of these inputs from the control module 102.

10) Vacuum LED

The Vacuum LED of the device 1002 is an output of the control module 102. The script uses the API as specified in the API module 706 to control its state.

The driver unit receives its power, control and status information via the control cable 1012 that connects to the medical device connector 308 of the universal control console 102. The device 1002 requires a vacuum to remove any excess fluid in the biopsy area and to pull tissue into the biopsy area for subsequent cutting. This vacuum is applied via the vacuum connector 1034 and controlled by the "vacuum" button 1104 or the script software depending on the state of the tool. Controlled RF power or a mechanical cutter may also be necessary for the device 1002 to cut through breast tissue. The RF power is applied through the RF cable connector 1026 and controlled by the footswitch 1014. Also the script software can inhibit the footswitch use or turn on the RF power without the footswitch. Whenever a sample of the tissue is desired, the "sample" button 1102 may be pressed to obtain the tissue sample.

There may be other components that are needed for the medical operation. For example, sterile water or saline line is needed for various surgical operations, and it can be provided through and controlled by the control console as well.

11) Flow Logic

Figure 10A:
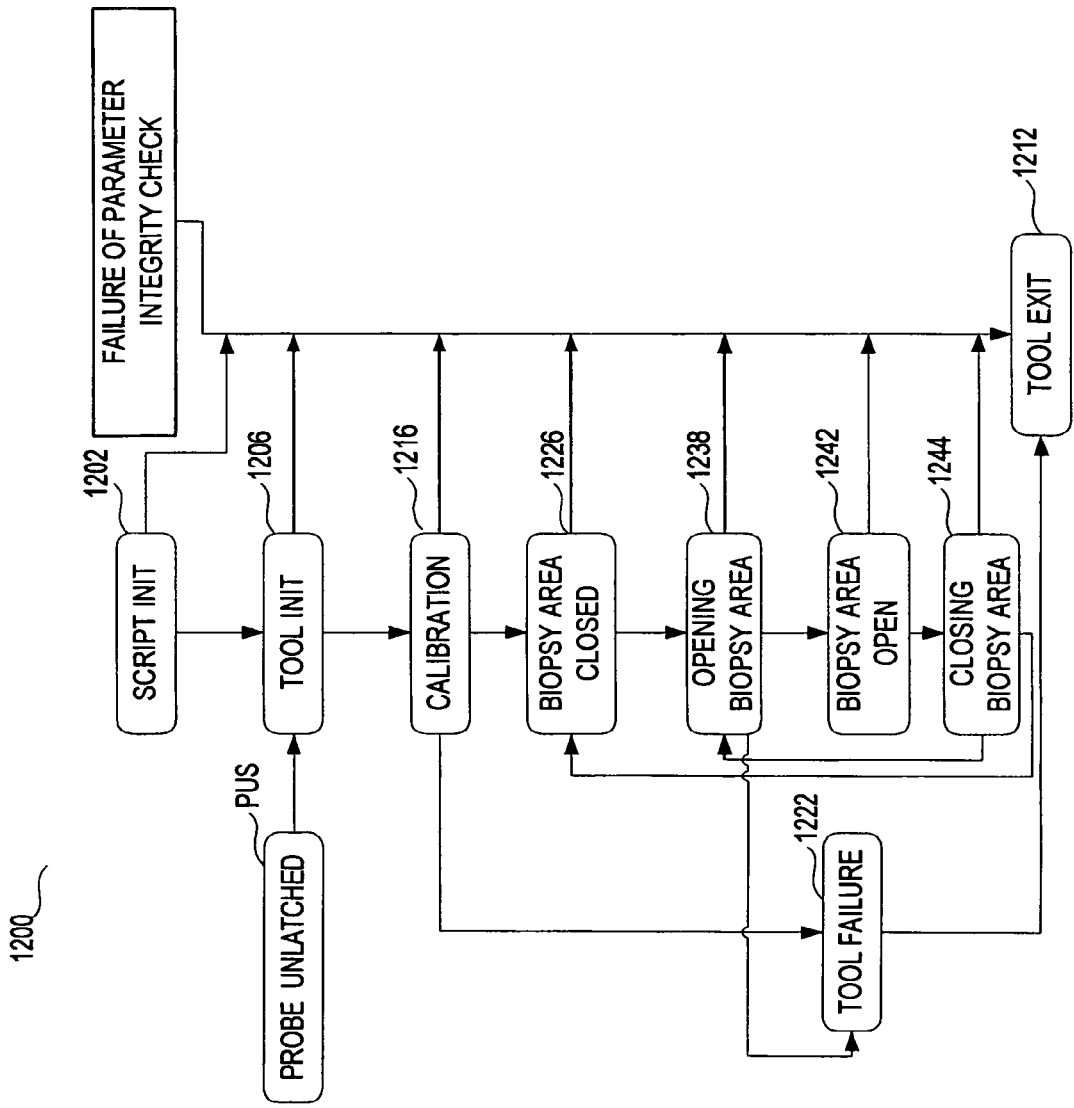
FIG. 10A presents a flowchart illustrating the operating states of the universal control console with the biopsy device in accordance with one example of the present invention.

FIG. 10A presents a flowchart 1200 covering the initial script initialization, normal surgical operation states, failure states, and tool exit states of the biopsy driver 1004 in operation with the universal control console 102 in accordance with one example of the present disclosure. Display screens are generated on the graphical display screen 304 of the universal control console 102 based on the state of the system. The system may display the status and user action information of the universal control console 102 and those of the medical device to the operator via various display screens during a surgical operation.

With reference to FIGS. 5, 6 and 10A, the display screens 602 through 616 cover from initial boot-up, medical device connection, utility mode setup, boot-up alarm sequence to the downloading of the medical device script. The specific states in FIG. 10A are unique to the biopsy driver 1004 operating with the universal control console 102 and are depicted in FIG. 5 as the flow 502. Any other medical device attached to the universal control console 102 may have unique states and display screens for their operation.

Figure 10B:
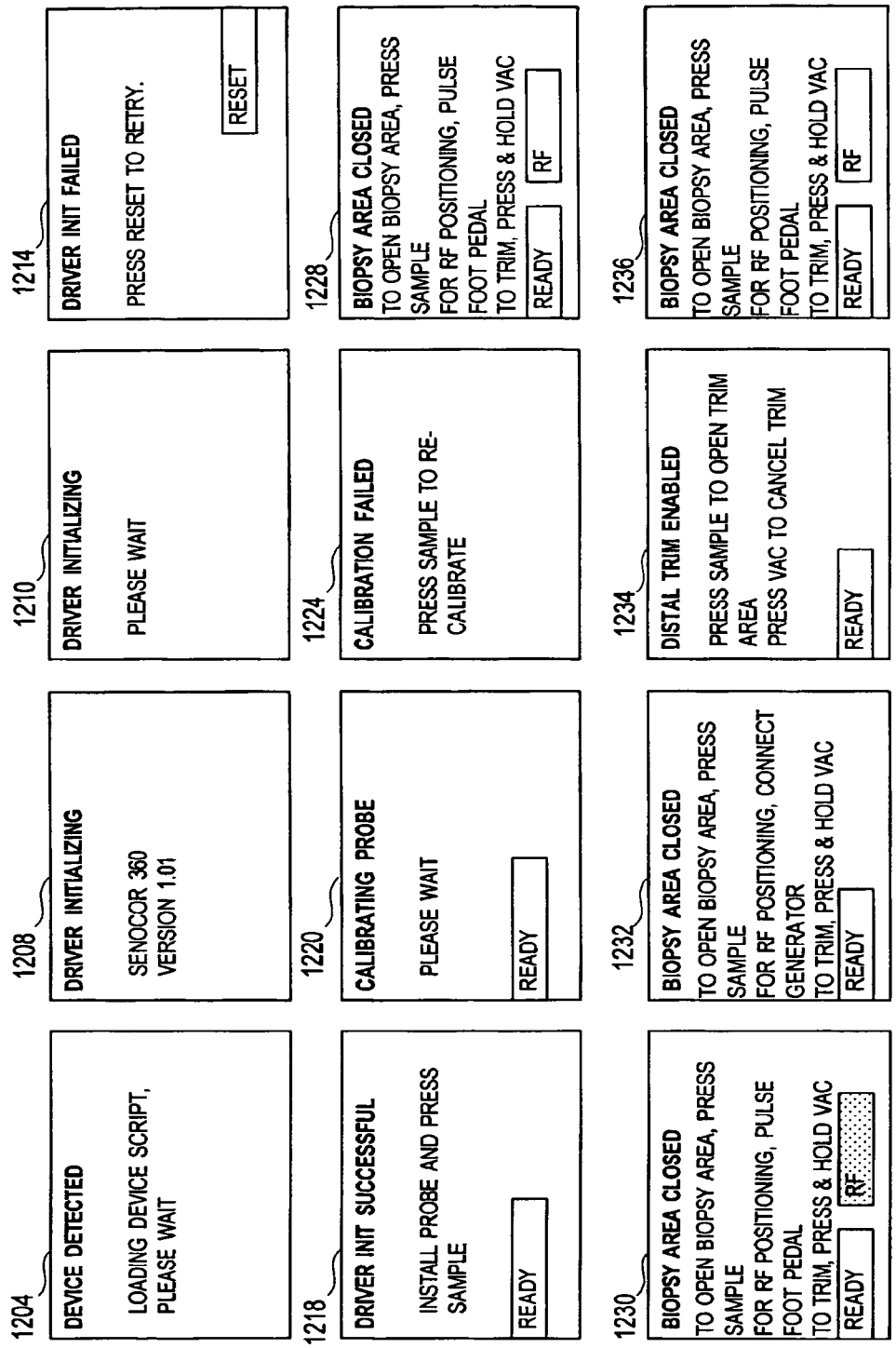
Figure 10D:
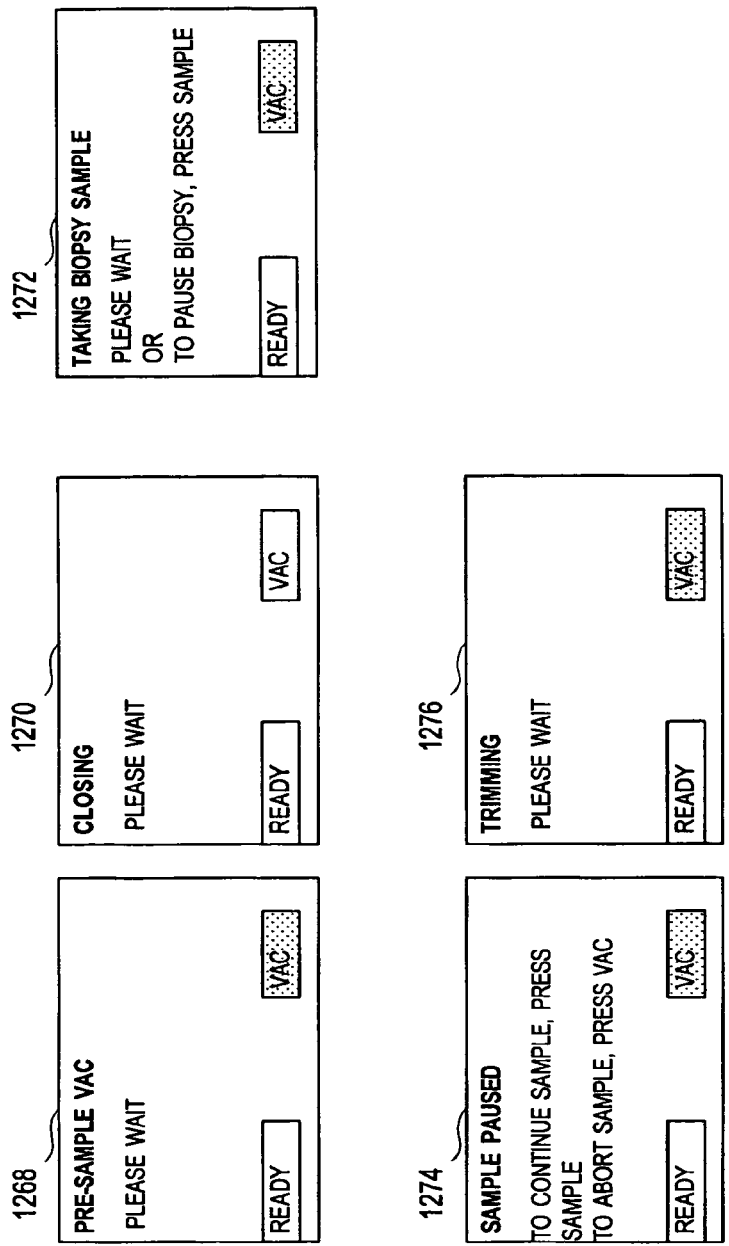

FIGS. 10B to 10D present various display screens in relation to states in FIG. 10A in accordance with one example of the present disclosure. With reference to FIGS. 10A to 10D, a script initialization state 1202 may have a display screen that looks like the screen 1204. In this state, initial system parameters, vacuum system parameters, and RF generator parameters are set. This state is initiated after the medical device script is downloaded to the universal control console. If this initialization is successful, the flow goes to a tool initialization state 1206, whose display screen may look like the screen 1208 or the screen 1210, if this is a subsequent initialization due to a reset. If the vacuum initialization fails in the script initialization state, the flow goes to a tool exit state 1212. If an error occurs, the script will exit to the appropriate error state.

In the tool initialization state 1206, tools are initialized without a probe inserted. The tool cycles the stroke motor, by ensuring that it operates at the full stroke and is left in the closed position. On the closing stroke the tool operates the cutting motor, thereby checking for its function. The tool polls the probe's phototransistors to ensure that a tool is not inserted. The tool polls the switches available to the user ("vacuum", "sample" and "foot switches") to ensure that none of them is pressed at the end of the cycle of the stroke motor, a situation that may indicate a stuck contact. If a probe is inserted during this state, the software exits to the tool failure state and may display a display screen 1214. If an error further occurs, the script will exit to the appropriate error state.

In the calibration state 1216, if the tool initialization state 1206 is successful, the screen 1218 is displayed while waiting for the surgical component such as a probe or a blade to be inserted. Once the probe is inserted, the calibration state 1216 first waits for the "sample" button to be pressed by the operator and then performs two short strokes to calibrate the tool, when the screen 1220 may be displayed. If an error occurs during calibration, such as when the stroke motor is not responding properly or the probe becomes unlatched, the script will exit to a tool failure state 1222 and displays the screen 1224. If an error further occurs, the script will exit to the appropriate error state.

If calibration is successful, the flow goes to a biopsy area closed state 1226. The biopsy area closed state 1226 first waits for the "sample" button to be pressed and then opens the cutter. In state 1226, the script performs the following functions:

1. Continually monitor for vacuum and generator system failures;
2. Continually monitor for new foot switch and Sample switch presses;
3. If a new footswitch press is detected and the "sample" button is not pressed, activate the RF Generator;
4. If the "vacuum" button is pressed and held for approximately one second, enable the distal trim and display the distal trim enabled screen;
5. If the "vacuum" button is pressed while distal trim is enabled, disable distal trim; and
6. If the "sample" button is pressed and the footswitch is not pressed, go to the opening biopsy area state 1238.

Some of the possible screens in the state 1226 are: screen 1228, wherein the biopsy area is closed and RF is inactive; screen 1230, wherein the biopsy area is closed but RF is active; screen 1232, wherein the biopsy area is closed and RF is disabled; screen 1234, wherein distal trim is enabled; and screen 1236, wherein the biopsy area is closed, RF is inactive and the footswitch is still pressed from previous RF activation.

The state 1226 typically goes to the state 1238 when the "sample" button is pressed. In the state 1238, the script performs an open stroke if the distal trim is not enabled and displays the screen 1240. It is understood that the operator may select a full or half stroke opening of a biopsy cutter, and some necessary GUI may be provided. When the open stroke is successfully completed, the flow goes to the biopsy area open state 1242. If an error occurs during the state 1238, such as when the stroke motor is not responding properly or probe becomes unlatched, the script will exit to the tool failure state 1222. If other errors further occur, the script will exit to the appropriate error state.

In the state 1242, the operator is allowed to activate the vacuum module or ESG module (e.g., if distal trim is not enabled). When the "sample" switch is pressed, the flow typically goes to the closing biopsy area state 1244. The ESG module is disabled if this state is entered from the probe unlatched state PUS, where the probe became unlatched during the close & cut processing of the state 1244.

In state 1242, the script performs the following functions:
1. RF is disabled if this state is entered from the state PUS, where the probe becomes unlatched during the close & cut processing of the closing biopsy area state. RF is also disabled if distal trim is enabled;

2. Continually monitor for failures from the vacuum and ESG modules;

3. Continually monitor for a new footswitch press, a new "vacuum" button press and a new "sample" button press;

4. If RF is not disabled, a new footswitch press is detected and the "sample" button is not pressed, activate the ESG module;

5. If the "vacuum" button is pressed and the "sample" button is not pressed, activate the vacuum module; and 6. If the "sample" button is pressed and the footswitch is not pressed, go to the closing biopsy area state.

Some of the possible screens in the state 1242 are: the screen 1246, which is displayed upon successful completion of the state 1238, or other states defaulting to the state 1242 even as the state 1242 is not explicitly listed; the screen 1248, which is displayed after fast-closing processing failed but biopsy area is subsequently opened; the screen 1250, which is displayed after entering from the state 1238 after the state 1244 and close and cut processing state have failed but biopsy area is subsequently opened; the screen 1252, which is displayed after entering from the completion of the state 1238 after the timer expired or the stroke motor has stopped during the state 1238; the screen 1254, which is displayed after entering from the state PUS, which is in turn entered from the state 1244 during the close and cut processing state; the screen 1256, which is displayed when ESG module is active; the screen 1258, which is displayed when the vacuum module is active; the screen 1260, which is displayed when entering from the successful completion of the state 1238, or other entry points not explicitly listed; the screen 1262, which is entered from the state 1238 after the state 1244 and the close and cut processing state have failed but biopsy area is subsequently opened; the screen 1264, which is entered from the completion of the state 1238 after the time expired or after the stroke motor has stopped during the state 1238; and the screen 1266, which is entered from the successful completion of the state 1238 when distal trim is enabled.

In state 1244, the vacuum module is activated for two seconds, and then the state 1244 starts the stroke motor to close the cutter and starts the cutting motor. If the "vacuum" button is pressed during the two-second vacuum period, the script will immediately start the stroke motor, at a rate faster than used when cutting, and will not start the cutting motor. When the close stroke is successfully completed, the flow goes to the state 1226. If an error further occurs, the script will exit to the appropriate error state.

In state 1244, the script performs the following operations:

1. If the distal trim is not enabled, turn on vacuum for 2 second pre-vacuum period;

2. If the "Sample" button is pressed during the pre-vacuum period, start the stroke motor at a fast rate to just close the cutter ("Fast Close"). If the Sample button was not pressed, or if the distal trim is enabled, start the stroke motor to close the cutter and start the cutting motor;

3. If the Sample button is pressed during a normal cutting operation (not a Fast Close), stop the motors, keeping the vacuum on. When the Sample button is pressed again, start both motors again; and 4. After the cutter has closed, if the distal trim is enabled, start the cutting motor in the opposite direction for a brief period to perform the distal trim.

Some of the possible screens in the state 1244 are: the screen 1268, which is displayed during pre-sample vacuum processing; the screen 1270, which is displayed during fast-closing processing; the screen 1272, which is displayed during close and cut processing; the screen 1274, which is displayed during the pause sample processing; and the screen 1276, which is displayed during distal trim processing. It is further understood that if in any one of the states 1216, 1222, 1226, 1238, 1242, 1244, a medical device such as the biopsy driver is removed, all these states are routed to state 1212.

Figures 11A, 11B:
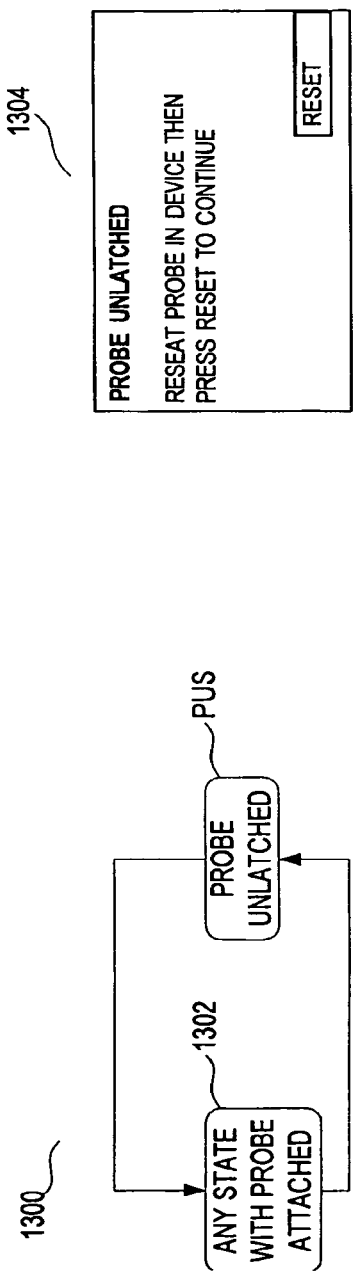
FIGS. 11A and 11B represent a probe failure processing flowchart and its corresponding display screen in accordance with one example of the present invention.

FIG. 11A presents a flowchart 1300 covering the unlatched probe processing state of the biopsy driver 1004 in operation with the universal control console 102 in accordance with one example of the present disclosure. When the probe is re-latched after being unlatched in the state PUS, the flow goes to a state 1302, where the flow will stay until the probe becomes unlatched, when the flow goes back to the state PUS.

The state PUS is entered from any operational (non-error) state that has a probe inserted in the device. The script prompts the user to reseat the probe as is displayed to the operator as screen 1278. In most cases, this state exits back to the state the script was in when the error occurred. The exception is if the script was in the state 1244, in either the pre-sample vacuum or close and cut processing. In those cases, the state PUS exits to the state 1242, with the ESG module disabled if the error occurred during the close and cut processing.

FIG. 11B presents a display screen in relation to the state PUS in FIG. 10A in accordance with one example of the present disclosure. The screen 1304 is displayed when the probe is unlatched, thereby requiring the operator to reseat the probe and reset the device.

Figure 12:
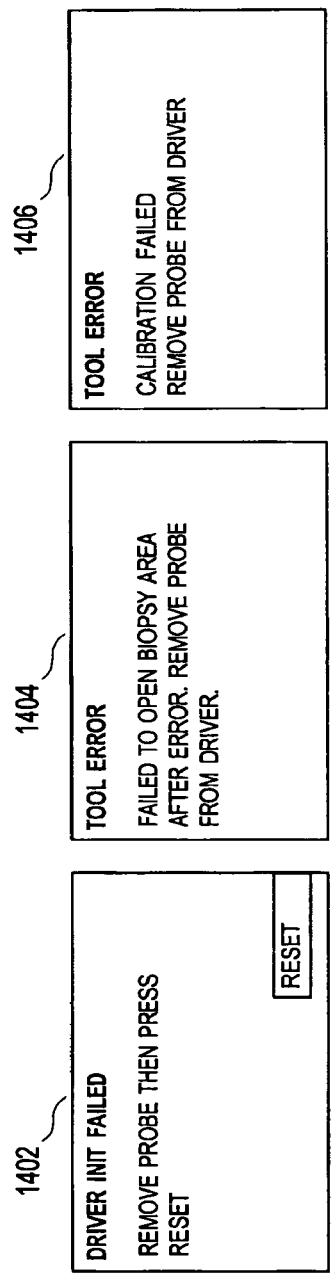
FIG. 12 present the display screens in the tool error state in accordance with one example of the present invention.

FIG. 12 presents various display screens in the tool failure state 1222 of the biopsy driver 1004 in operation with the universal control console 102 in accordance with one example of the present disclosure. The tool failure state is an error state that is entered when an error occurs that requires that the probe to be removed from the device. This state displays a message indicating the error that has occurred and then waits for probe to be removed. Various screens are displayed in the tool failure state: the screen 1402, when a probe was inserted in the device during the state 1206; the screen 1404, after a biopsy has failed and the subsequent states 1238 also failed; and the screen 1406, after calibration has failed and open stroke has failed to complete.

Figures 13A, 13B:
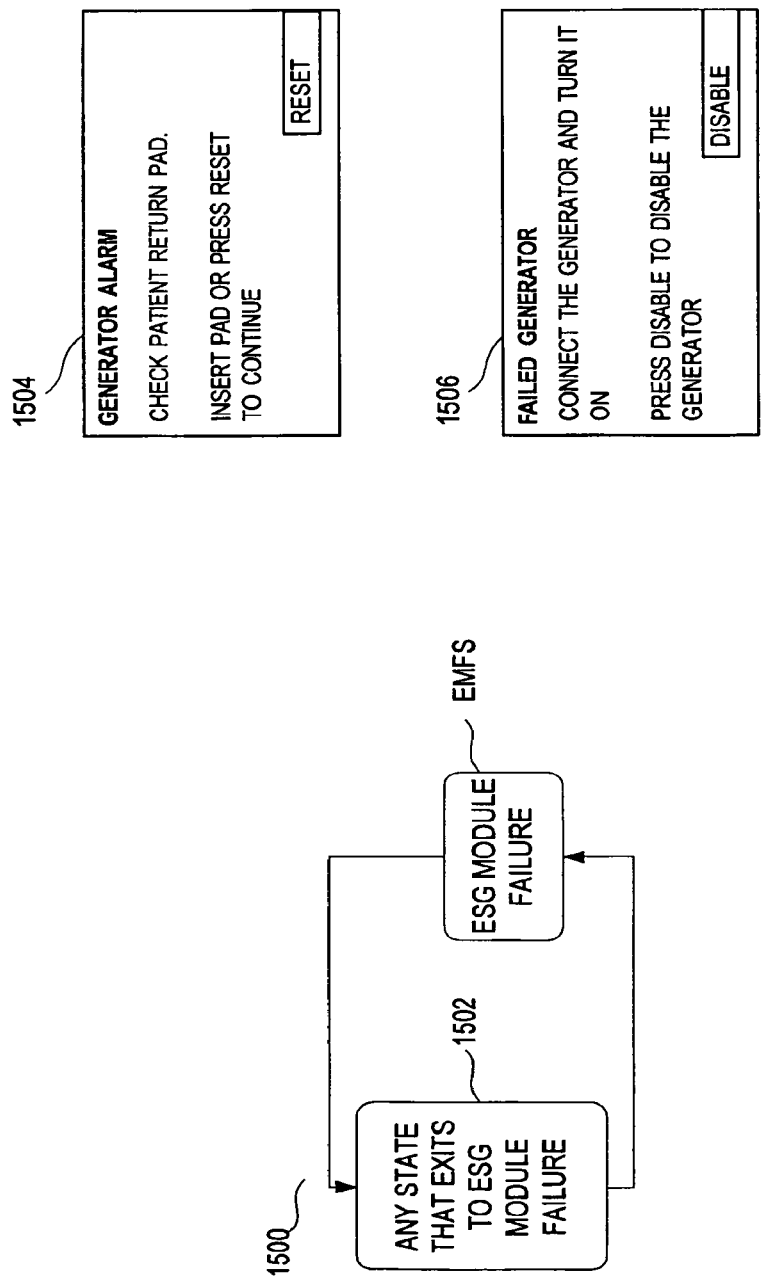
FIGS. 13A and 13B present a ESG failure processing flowchart and its corresponding display screens in accordance with one example of the present invention.

FIG. 13A presents a flowchart 1500 covering the ESG module failure states (EMFS), whose display screens are further illustrated in FIG. 13B, of the biopsy driver 1004 in operation with the universal control console 102 in accordance with one example of the present disclosure. When the ESG module failure is corrected after being triggered in the state EMFS, the flow goes to a state 1502, where the flow will stay until the ESG module failure is triggered again, when the flow goes back to the state EMFS.

With reference to both FIGS. 13A and 13B, the state EMFS is entered from any state, except the states 1202 and 1212, when the system detects a failure in the system. The script supports two types of ESG modules and the detection of a failure depends upon the ESG module type. The absence of any ESG module connected causes an ESG module failure. In addition, if a Type-C generator is detected, a failure is caused when it does not respond or if the patient pad is not connected when required. (It is required during calibration state and whenever ESG RF is activated.) The following screens are displayed in the ESG module failure state: the screen 1504, which is displayed when there is a patient pad failure; and the screen 1506, which is displayed when there is an ESG module failure.

Figures 14A, 14B:
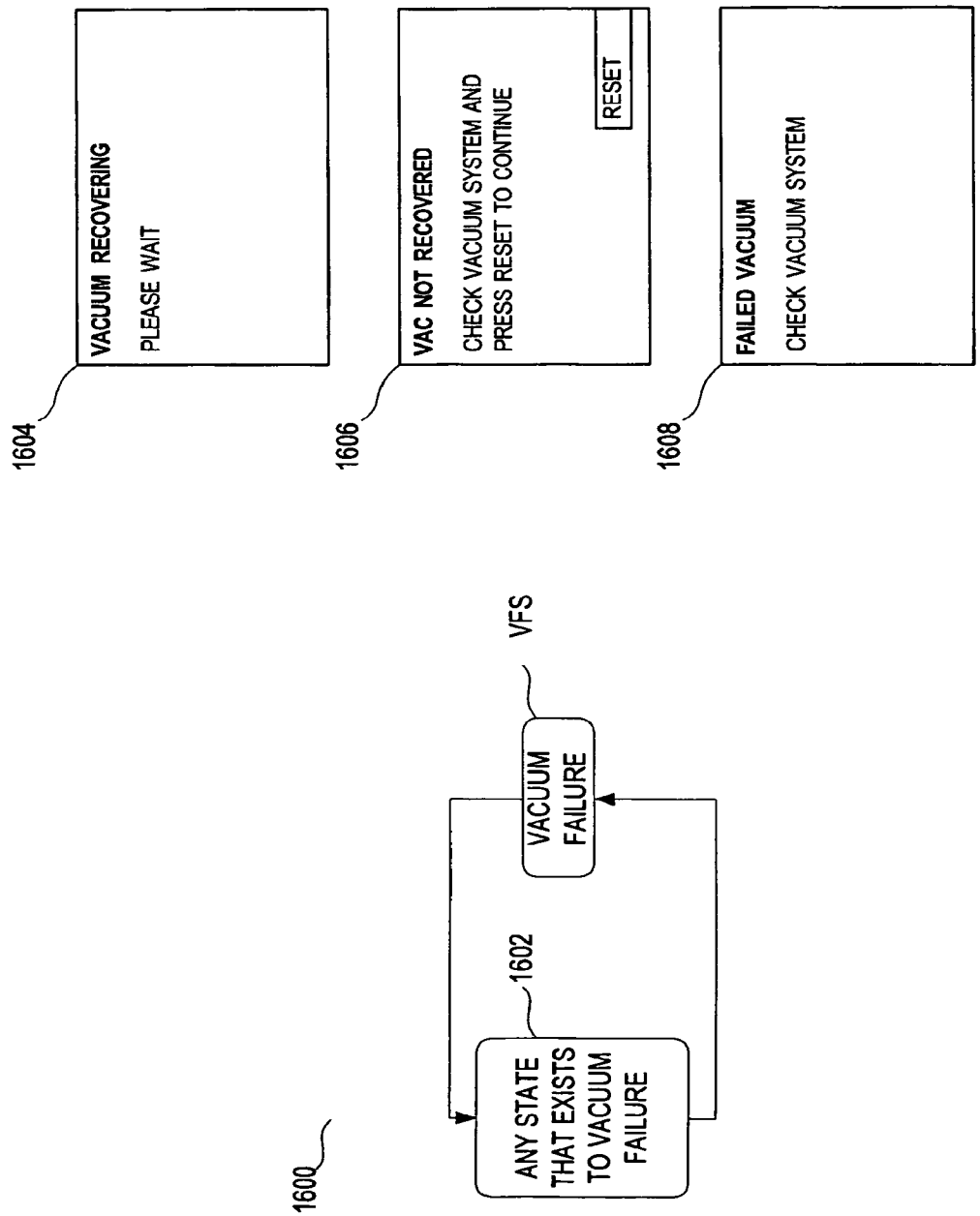
FIGS. 14A and 14B present a vacuum failure processing flowchart and its corresponding display screens in accordance with one example of the present invention.

FIG. 14A presents a flowchart 1600 covering the vacuum failure states (VFS), whose display screens are further illustrated in FIG. 14B, of the biopsy driver 1004 in operation with the universal control console 102 in accordance with one example of the present disclosure. When the vacuum failure is corrected after being triggered in the state VFS, the flow goes to a state 1602, where the flow will stay until the vacuum failure is triggered again, when the flow goes back to the state VFS.

With reference to both FIGS. 14A and 14B, the state VFS is entered from most states when the system detects a failure in the vacuum module. The failure may be a result of the unavailability of the vacuum module (it becomes disconnected) or of a vacuum level that does not meet the minimum requirements. The script will wait for eight seconds to allow the vacuum module to recover, and may turn off the vacuum module and require the operator to press the "reset" button to continue.

The following screens are displayed in the vacuum failure state: the screen 1604, which is displayed while the vacuum is recovering; the screen 1606, which is displayed after the vacuum is not recovered; and the screen 1608, which is displayed after vacuum has failed to recover.

Figure 15A:
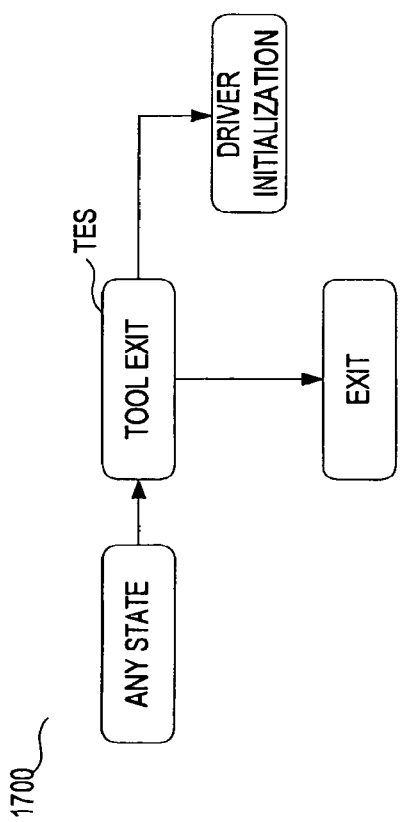
FIGS. 15A and 15B present a tool exit processing flowchart and its corresponding display screens in accordance with one example of the present disclosure.
Figure 15B:
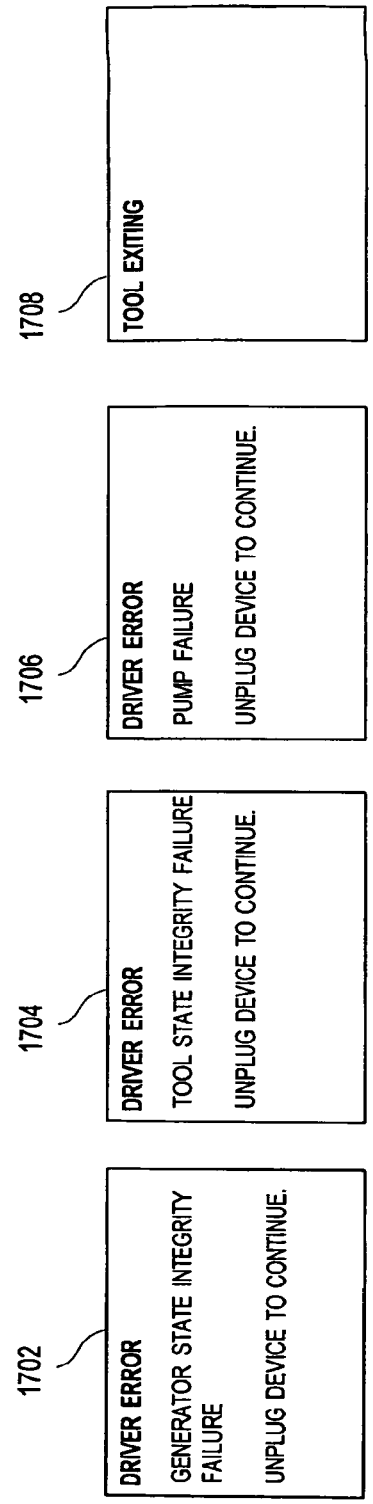

FIG. 15A presents a flowchart 1700 covering the exit processing states, whose display screens are further illustrated in FIG. 15B, of the biopsy driver 1004 in operation with the universal control console 102 in accordance with one example of the present disclosure. When the driver is removed from any state, the tool exit state TES is triggered. Typically, if the time expires, or the ESG module is reconfigured, the flow goes back to a prior menu screen. If the driver is reconnected, the flow goes to the state 1206.

The following screens are displayed in the tool exit state: the screen 1702, which is displayed after an integrity check for the ESG module has failed; the screen 1704, which is displayed after an integrity for the tool has failed; the screen 1706, which is displayed after the pump fails to initialize; and the screen 1708, which is displayed after the tool script exits normally.

The above disclosure provides many different embodiments or examples for implementing different features of the disclosure. Specific examples of components and processes are described to help clarify the disclosure. These are, of course, merely examples and are not intended to limit the disclosure from that described in the claims.

Although the invention is illustrated and described herein as embodied in a design and method for a universal reusable medical equipment control module, it is nevertheless not intended to be limited to the details shown, since various modifications and structural changes may be made therein without departing from the spirit of the invention and within the scope and range of equivalents of the claims. Accordingly, it is appropriate that the appended claims be construed broadly and in a manner consistent with the scope of the disclosure, as set forth in the following claims.

What is claimed is:

1. A control console for controlling a variety of electrically powered medical devices, comprising:
a device connecting module configured to communicate with each of a biopsy medical device and non-biopsy medical device; and
a microprocessor based control module coupled to the device connecting module, the microprocessor based control module configured to direct an operation of the biopsy medical device based on communications from the biopsy medical device and configured to control one or more functions of the non-biopsy medical device based on communications from the non-biopsy medical device.

2. The control console of claim 1, wherein the non-biopsy medical device is one of a temperature probe, a heart rate monitor device, a drug infusion tool, and an anesthesia tool.

3. The control console of claim 1, wherein the biopsy medical device includes at least one radio frequency or mechanically energized tool.

4. The control console of claim 1, further comprising at least one peripheral module associated with the biopsy medical device, wherein the control module is communicatively interposed between the at least one peripheral module and the biopsy medical device.

5. The control console of claim 4, wherein the at least one peripheral module is controlled by the biopsy medical device.

6. The control console of claim 4, wherein the at least one peripheral module is a footswitch module.

7. The control console of claim 4, wherein the at least one peripheral module is a vacuum pump module.

8. The control console of claim 4, wherein the at least one peripheral module is a fluid pump module.

9. The control console of claim 1, further comprising a software module configured to receive a predetermined software script from at least one of the biopsy medical device and the non-biopsy medical device for operating the same.

10. The control console of claim 1, wherein the device connecting module wirelessly communicates with each of a biopsy medical device and the non-biopsy medical device.

11. A multi-device control console for controlling a biopsy probe and at least one other medical device, the control console comprising:
a plurality of connecting modules for communicating with the biopsy probe and the at least one other medical device;
one or more connecting modules for communicating with one or more peripheral modules required to be operated with the biopsy probe and the at least one other medical device;
a microprocessor based control module for controlling an operation of the biopsy probe and the at least one other medical device with the peripheral modules, and
a software module for controlling logical and interface functions of the operation of the biopsy probe and the at least one other medical device with the peripheral modules,
whereby the software module is arranged to receive and process a predetermined software script from the biopsy probe and the at least one other medical device for operating the same and for displaying information relevant to the biopsy probe and the at least one other medical device on a graphical user interface.

12. The control console of claim 11, wherein at least one of the peripheral modules is an electro surgical generation module.

13. The control console of claim 11, wherein at least one of the peripheral modules is a footswitch module.

14. The control console of claim 11, wherein at least one of the peripheral modules is a fluid pump module.

15. The control console of claim 11, wherein the control console further comprises an operator module including one or more indicators.

16. The control console of claim 11, further comprising a power module.

17. The control console of claim 11, wherein the control module controls the operation of the medical device through wireless communication links.

18. The control console of claim 11, wherein the control module controls the operation of the medical device through wired communication connections.

19. The control console of claim 11, wherein the control module controls the operation of the medical device through digital signals.

20. The control console of claim 11, wherein the control module controls the operation of the medical device through analog signals.

* * * * *

UNITED STATES PATENT AND TRADEMARK OFFICE
CERTIFICATE OF CORRECTION

| | | |
|---|---|---|
| PATENT NO. | : 10,912,541 B2 | Page 1 of 1 |
| APPLICATION NO. | : 14/161218 | |
| DATED | : February 9, 2021 | |
| INVENTOR(S) | : Richard L. Quick et al. | |

It is certified that error appears in the above-identified patent and that said Letters Patent is hereby corrected as shown below:

In the Specification

At Column 1, Line 9:
10/847,699, filed May 17, 2004, which is related to, and
Should be:
---10/847,699, filed May 17, 2004, abandoned, which is related to, and---

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*